United States Patent
Barclay Dupere et al.

(10) Patent No.: US 10,869,886 B2
(45) Date of Patent: Dec. 22, 2020

(54) CELL SUSPENSION FOR USE IN THE TREATMENT OF LOWER EXTREMITY PERIPHERAL ARTERY DISEASE

(71) Applicants: Rexgenero Biosciences S.L., Seville (ES); Servicio Andaluz de Salud, Seville (ES); Fundación Pública Andaluza Progreso y Salud, Seville (ES)

(72) Inventors: Jonathan Robert Barclay Dupere, Brighton (GB); Liesbeth de Jong, Seville (ES); Edwin J. Wagena, Brighton (GB); Inmaculada Concepción Herrera Arroyo, Cordova (ES)

(73) Assignees: REXGENERO BIOSCIENCES S.L., Seville (ES); SERVICIO ANDALUZ DE SALUD, Seville (ES); FUNDACIÜBLICA ANDALUZA PROGRESO Y SALUD, Seville (ES)

( * ) Notice: Subject to any disclaimer, the term of this patent is extended or adjusted under 35 U.S.C. 154(b) by 222 days.

(21) Appl. No.: 15/688,555

(22) Filed: Aug. 28, 2017

(65) Prior Publication Data
US 2018/0055884 A1   Mar. 1, 2018

(51) Int. Cl.
| | | |
|---|---|---|
| *A61K 35/17* | (2015.01) | |
| *C12N 5/078* | (2010.01) | |
| *C12N 5/0789* | (2010.01) | |
| *A61K 35/15* | (2015.01) | |
| *A61K 35/28* | (2015.01) | |
| *A61K 35/12* | (2015.01) | |

(52) U.S. Cl.
CPC ............. *A61K 35/17* (2013.01); *A61K 35/15* (2013.01); *A61K 35/28* (2013.01); *C12N 5/0634* (2013.01); *C12N 5/0647* (2013.01); *A61K 2035/124* (2013.01)

(58) Field of Classification Search
None
See application file for complete search history.

(56) References Cited

U.S. PATENT DOCUMENTS

2011/0076255 A1   3/2011   Pecora et al.

OTHER PUBLICATIONS

Belaj et al., "Association of the Derived Neutrophil-Lymphocyte Ratio With Critical Limb Ischemia", Angiology. Apr. 2016; 67(4): 350-354. Epub Jun. 9, 2015.

Gary et al., "Neutrophil-to-Lymphocyte Ratio and Its Association with Critical Limb Ischemia in PAOD Patients", PLoS One. 2013; 8(2): e56745. Epub Feb. 15, 2013.

Gary et al., "Platelet-to-Lymphocyte Ratio: A Novel Marker for Critical Limb Ischemia in Peripheral Arterial Occlusive Disease Patients", PLoS One. Jul. 2, 2013; 8(7): e67688.

Gary et al., "Lymphocyte-to-monocyte ratio: a novel marker for critical limb ischemia in PAOD patients", Int J Clin Pract. Dec. 2014; 68(12): 1483-1487. Epub Oct. 31, 2014.

Hirsch et al, "ACC/AHA 2005 Practice Guidelines for the management of patients with peripheral arterial disease (lower extremity, renal, mesenteric, and abdominal aortic): a collaborative report from the American Association for Vascular Surgery/Society for Vascular Surgery, Society for Cardiovascular Angiography and Interventions, Society for Vascular Medicine and Biology, Society of Interventional Radiology, and the ACC/AHA Task Force on Practice Guidelines (Writing Committee to Develop Guidelines for the Management of Patients With Peripheral Arterial Disease): endorsed by the American Association of Cardiovascular and Pulmonary Rehabilitation; National Heart, Lung, and Blood Institute; Society for Vascular Nursing; TransAtlantic Inter-Society Consensus; and Vascular Disease Foundation", Circulation. Mar. 21, 2006; 113(11): e463-654.

Lambert et al., "Medical management of critical limb ischaemia: where do we stand today?", J Intern Med. Oct. 2013; 274(4): 295-307. Epub Jul. 22, 2013.

Lawall et al., "Treatment of peripheral arterial disease using stem and progenitor cell therapy", J Vasc Surg. Feb. 2011; 53(2): 445-453. Epub Oct. 27, 2010.

Peeters Weem et al., "Bone Marrow derived Cell Therapy in Critical Limg Ischemia: A Meta-analysis of Randomized Placebo Controlled Trials", Eur J Vasc Endovasc Surg. Dec. 2015; 50(6): 775-783. Epub Oct. 12, 2015.

Thiruvoipati et al., "Peripheral artery disease in patients with diabetes: Epidemiology, mechanisms, and outcomes", World J Diabetes. Jul. 10, 2015; 6(7): 961-969.

International Search Report dated Oct. 4, 2017, in International Patent Application No. PCT/EP2017/071580, 7 pages.

*Primary Examiner* — Robert M Kelly
(74) *Attorney, Agent, or Firm* — Squire Patton Boggs (US) LLP

(57) ABSTRACT

The present invention refers to a cell suspension of autologous or allogeneic, preferably autologous, adult bone marrow-derived white blood cells, preferably derived from the crest of the ilium (or iliac crest), enriched for mononuclear cells, meaning more than 25% of the white blood cells (WBCs) present in the cell suspension are mononuclear cells, and comprising:
 A. Mononuclear cells (MNC) selected from the list comprising or consisting of:
  i. A population of Lymphocytes;
  ii. A population of Monocytes; and
  iii. A population of Hematopoietic stem cells expressing CD34;
and wherein the cell suspension further comprises:
 B. Granulocytes;
for use in the treatment or amelioration of lower extremity peripheral artery disease.

11 Claims, 6 Drawing Sheets

FIGURES

6A Longitudinal growth of arteries    6B. New vessels in an area

6C.

CELL SUSPENSION FOR USE IN THE TREATMENT OF LOWER EXTREMITY PERIPHERAL ARTERY DISEASE

TECHNICAL FIELD

The present invention relates to a cell suspension of adult bone marrow derived cells which can be used in the treatment or amelioration of lower extremity peripheral artery disease, preferably critical ischemia limb.

BACKGROUND OF THE INVENTION

Lower extremity Peripheral Artery Disease (PAD) includes a wide range of vascular diseases caused by atherosclerotic, thromboembolic, and inflammatory processes that alter the structure and function of the lower limb arteries. The primary cause of PAD, however, is atherosclerosis.

Symptomatic lower extremity PAD results from inadequate blood flow leading to insufficient oxygen supply. PAD is associated with atherothrombosis of other vascular beds, including the cardiovascular and cerebrovascular systems. The presence of diabetes mellitus (hereinafter DM) greatly increases the risk of PAD, accelerates the course of the disease, making diabetes patients more susceptible to ischemic events, impaired vascular function, increased morbidity and mortality and impaired Quality of Life (QoL) (Thiruvoipati et al, 2015). Indeed, PAD patients are regarded as a heterogeneous group of patients ranging from asymptomatic to patients with Intermittent Claudication (IC) and patients with CLI (critical limb ischemia). CLI refers to a state of arterial insufficiency that reduces distal perfusion pressure to such an extent that microcirculation and blood flow to tissues and nutrition are severely disturbed. Minor trauma, ulceration, and infection may co-exist increasing the metabolic demands of the affected tissue often leading to chronic, non-healing ulcers. It is a progressive disease characterized by multilevel disease, high burden of comorbidity and limited life span.

Although ankle brachial index (ABI) is used to diagnose PAD and is an indicator of PAD severity, it does not fully correlate with the clinical severity of the disease. A broader range of clinical symptoms are therefore used to classify the severity of PAD with two classification systems routinely used in clinical practice: Rutherford and Fontaine (Hirsch A T, 2006). The clinical severity of PAD ranges from asymptomatic to gangrene and limb ischemia requiring amputation. PAD is a progressive disease with the severity of the condition increasing over time. Disease progression is more rapid in patients with DM.

Grading the symptoms of PAD and the anatomic lesions responsible for these symptoms provides an objective measure by which to follow subjects clinically, and, importantly, provides consistency when comparing medical and interventional treatment strategies in clinical studies.

Rutherford classification is a commonly-used clinical staging system for describing PAD and is similar to the Fontaine classification, but is more commonly cited in newer publications in the field of Vascular Medicine. Peripheral artery occlusive disease is commonly divided in the Fontaine stages, introduced by Rene Fontaine in 1954 from Stage I (asymptomatic) to Stage IV (ulceration or gangrene). A classification introduced by Rutherford in 1986 and revised in 1997 consists of four grades and seven categories, ranging from Category 0 (asymptomatic) to Category 6 (severe ischemic ulcers or gangrene) (Table 1).

TABLE 1

Fontaine and Rutherford classification of PAD

| Fontaine Classification | | Rutherford Classification | | | |
|---|---|---|---|---|---|
| Fontaine Grade | Clinical description | Rutherford Grade | Rutherford Category | Clinical description | Objective criteria |
| I | Asymptomatic | 0 | 0 | Asymptomatic-no hemodynamically significant occlusive | Normal treadmill or reactive hyperaemia test |
| II-a | Intermittent claudication after more than 200 meters of | I | 1 | Mild claudication | Completes treadmill exercise[†]; AP after exercise > 50 mm Hg but at least 20 mm Hg lower than resting |
| II-b | Intermittent claudication after less than 200 meters of | I | 2 3 | Moderate claudication Severe claudication | Between Categories 1 and 3 Cannot complete standard treadmill exercise[†] and AP after exercise < 50 mm Hg |
| III | Rest pain | II* | 4 | Ischemic rest pain | Resting AP < 40 mm Hg, flat or barely pulsatile ankle or |
| | | | 5 | Minor tissue loss-non-healing ulcer, focal gangrene with | Resting AP < 60 mm Hg, ankle or metatarsal PVR flat or barely pulsatile; TP < 40 mm |
| IV | Ulceration or gangrene | III* | 6 | Major tissue loss-extending above TM level, functional foot | Same as Category 5 |

*Grades II and III, Categories 4, 5, and 6, are embraced by the term chronic critical ischemia.
[†]Five minutes at 2 mph on a 12% incline.
AP = Ankle pressure; PVR = pulse volume recording; TP = toe pressure; TM = trans-metatarsal.

CLI is a progressive disease characterized by multi-level disease, high burden of comorbidity and limited life span. The Trans-Atlantic Inter-Society Consensus (TASC) Document on Management of Peripheral Arterial Disease II, 2007 (TASCII, 2007), recommends that the term CLI should be used for all subjects with chronic ischemic rest pain, ulcers or gangrene attributable to objectively proven arterial occlusive disease. The current definition of CLI includes subjects with lower-extremity rest pain, ulcers or gangrene secondary to severely compromised blood flow in the limb persisting for more than two weeks. It constitutes Rutherford Categories 4-6 (ischemic rest pain, minor tissue loss, and major tissue loss respectively) or Fontaine Grade III and IV.

The only treatment of the underlying disease in CLI is revascularization. However, a significant proportion of the population (estimated at between 50% and 90% of the population) is not suitable for manual revascularization (surgical bypass or endovascular procedure), due either to the absence of viable blood vessels, the failure of previous manual re-vascularization procedures or comorbidities. Many patients with CLI have multiple conditions which may prevent them from undergoing manual revascularization. Ultimately, amputation is often the only remaining option for a large proportion of these patients, where the aim is to manage intractable pain, prevent progression of gangrene or combat infection. New therapies are therefore urgently needed.

Currently, the initial treatment for patients with CLI typically consists of an assessment of the affected (index) limb for suitability to be re-vascularized either with a surgical bypass or using endovascular methods. All patients will be treated for existing symptoms of the disease, particularly pain, ulcers and infections. Pain management however is very often ineffective and since ischemic ulcers rarely heal, wound management is usually focused on infection control, prevention of deterioration and limb salvage. The overall treatment goals for CLI include:

Pain control.
Wound healing.
Limb salvage.
Improvement of QoL, including maintaining ambulatory state.
Reduction of overall cardiac risk.

The cell suspension of the present invention is especially indicated for CLI patients, particularly for CLI patients with DM who have no option for revascularization using surgical bypass or endovascular methods. For these patients the unmet need is highest as there are no therapeutic options to treat the underlying disease. Any treatment used in these patients is symptomatic: wound care, infection control and pain management. For those patients unsuitable for manual revascularization, as the disease progresses, the only clinical option may be amputation either in response to progressive gangrene, uncontrolled infection or intractable pain. Of the PAD patients who develop CLI, approximately 25% die within a year (NICE, 2012). Dependent on the severity of the CLI, one-year primary amputation rates range from 5% to 40%, with the highest rates in patients who are not suitable for revascularization, who are neurologically impaired or non-ambulatory.

BRIEF DESCRIPTION OF THE INVENTION

Figure 1:
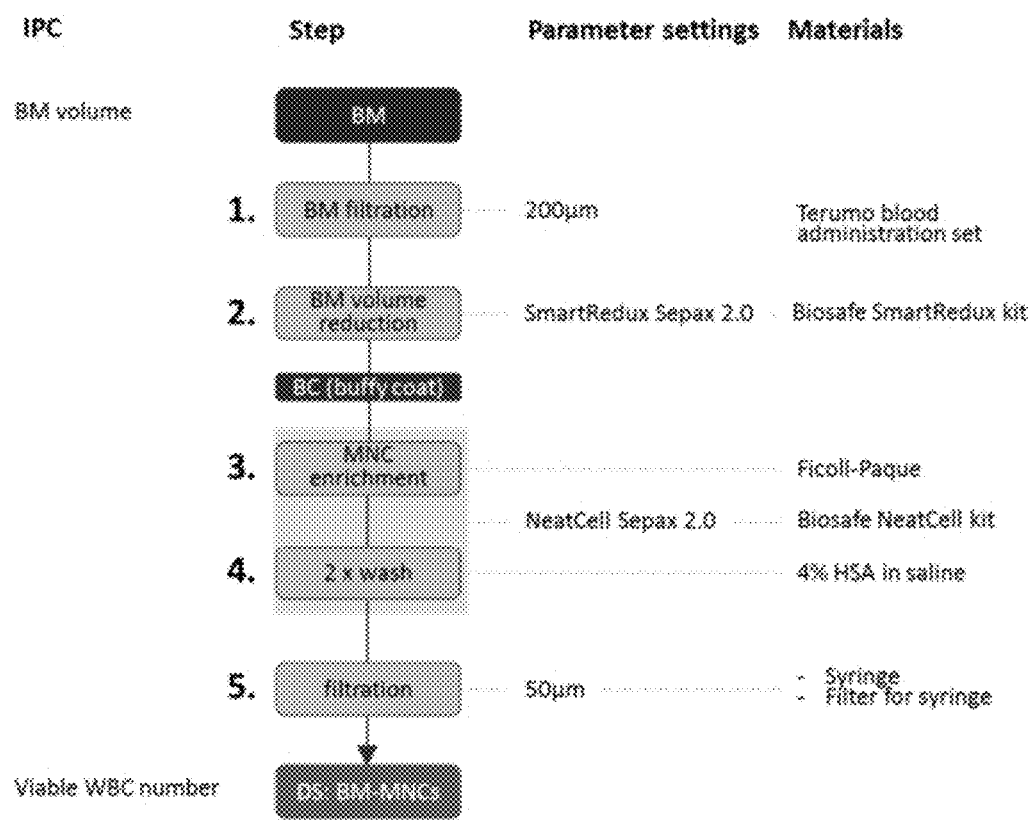
FIG. 1. Flow chart of manufacturing of the cell suspension of the invention.

The problem addressed by the present invention is to provide patients suffering from lower extremity Peripheral Artery Disease (PAD), preferably CLI patients, more preferably CLI patients with DM who have no option for revascularization using surgical bypass or endovascular methods, with an improved therapeutic alternative. Such therapeutic improved alternative is provided by the present invention in the form of a cell suspension of autologous or allogeneic adult bone marrow derived cells as defined by the aspects and preferred embodiments referred to below.

Therefore, a first aspect of the invention refers to a cell suspension (from hereinafter "cell suspension of the invention") of autologous or allogeneic, preferably autologous, adult bone marrow-derived white blood cells, preferably derived from the crest of the ilium (or iliac crest), enriched for mononuclear cells, meaning more than 25% of the white blood cells (WBCs) present in the cell suspension are mononuclear cells, and comprising:

A. Mononuclear cells (MNC) selected from the list comprising or consisting of:
  i. A population of Lymphocytes;
  ii. A population of Monocytes; and
  iii. A population of Hematopoietic stem cells expressing CD34;
and wherein the cell suspension further comprises:
B. Granulocytes;
for use in the treatment or amelioration of lower extremity peripheral artery disease.

It is noted that, in general terms, the cell populations A) and B) in turn comprise a cell population that expresses CXCR4, a receptor for the migration factor SDF1, from this population it is important to point out the presence of a subpopulation of hematopoietic stem cells expressing CD34 and CXCR4. In addition, the cell populations A) and B) in turn comprise a further cell population that expresses VEGFR2, a receptor for angiogenesis factor VEGF that is involved in angiogenesis and vasculogenesis.

Lastly, the cell population A. iii) in turn comprises a cell population that does not express CD38, which are early non-committed haematopoietic stem cells.

It is noted that mononuclear cells (MNCs) are considered the primary active component of the cell suspension of the invention. In particular, the active components or ingredients of the cell suspension of the present invention are MNCs selected from the list consisting of lymphocytes, monocytes and hematopoietic stem cells which express CD34, more particularly the subpopulations of early, non-committed hematopoietic stem cells which express CD34 and do not express CD38, white blood cells capable of SDF-1 mediated migration, which express CXCR4, stem cells capable of SDF-1 mediated migration, which express CD34 and CXCR4 and white blood cells capable of angiogenesis, which express VEGFR2. All of these mononuclear cells are bone marrow derived cells, preferably derived from the crest of the ilium (or iliac crest).

In addition, it is further noted that the white blood cell suspension of the invention further comprises granulocytes, which are neutrophils, eosinophils and/or basophils. In this regard, it is important to note that the final cell suspension product of the invention as illustrated in the examples, is dosed based on viable white blood bone-marrow derived cells, including not only the MNC white blood cell fraction (lymphocytes and monocytes and stem cells) but also granulocytes.

In a preferred embodiment of the first aspect of the invention, the cell suspension of the invention, in the final formulation which is enriched for mononuclear cells, meaning more than 25% of the total number of white blood cells (WBCs) present in the cell suspension are mononuclear cells, comprises from about $4 \times 10^8$ to about $2 \times 10^9$, autologous or allogeneic white blood bone marrow-derived cells, preferably autologous, preferably derived from the crest of the ilium (or iliac crest), wherein of the total number of from about $4 \times 10^8$ to about $2 \times 10^9$ of white blood cells,
  i. About 20% to about 51% are lymphocytes, and about 3.9% to about 22.3% are monocytes;
  ii. about 1.4% to about 10% are hematopoietic stem cells that express CD34;
  iii. about 25.3% to about 83.3%, preferably from about 32.3% to about 80.0%, of the total number of white blood cells are mononuclear cells, preferably selected from the list consisting of lymphocytes, monocytes and CD34 cells;
  iv. about 16.7% to about 74.7%, preferably about 20.0% to about 67.7%, are granulocytes
  v. Of the total number of hematopoietic stem cells that express CD34, about 7.7% to about 55.5% are early, non-committed hematopoietic stem cells that do not express CD38;
  vi. about 5.4% to about 38.8% of the white blood cells express CXCR4;
  vii. Of the total number of hematopoietic stem cells that express CD34, about 0.7% to about 10.3% are stem cells that express CD34 and CXCR4;
  viii. about 0.07% to about 24.7% of white blood cells express VEGFR2; and
  ix. The maximum ratio of red blood cells to leucocyte cells is 6.7 and the maximum ratio of platelets to leucocyte cells is 32.

In another preferred embodiment of the first aspect of the invention, the cell suspension of the invention, in the final formulation, as defined in the precedent paragraph, comprises from about $4 \times 10^8$ to about $1.2 \times 10^9$ white blood cells, more preferably from about $5 \times 10^8$ to about $2 \times 10^9$ white blood cells, still more preferably from about $5 \times 10^8$ to about $1.2 \times 10^9$ white blood cells, and all dosage values between each of the above listed values.

Certain embodiments may be selected as sub-ranges from these values of white blood cells in the final formulation. For example, a specific embodiment may be selected as a white blood cell content, in the final formulation, of above $8 \times 10^8$ to about $1.2 \times 10^9$ white blood cells. Another example of how a range may be selected in an embodiment would be the selection of a content of about $9 \times 10^8$ to about $1.1 \times 10^9$ white blood cells. A third example of ranges that may be selected for a specific embodiment would be the selection of about $9.5 \times 10^8$ to about $1.05 \times 10^9$ white blood cells. A fourth example of ranges that may be selected for a specific embodiment would be selection of a content such as above $9.8 \times 10^8$ to about $1.02 \times 10^9$ white blood cells.

Other examples of how a range of an embodiment of content or dosed may be selected include a range of from above $6 \times 10^8$ to about $2 \times 10^9$, preferably to about $1.2 \times 10^9$, white blood cells, encompassing all dosage values in-between. Another example would be the selection of a range of from above $7 \times 10^8$ to about $2 \times 10^9$, preferably to about $1.2 \times 10^9$, white blood cells, encompassing all dosage values in-between. Another example would be the selection of a range of from above $8 \times 10^8$ to about $2 \times 10^9$, preferably to about $1.2 \times 10^9$, white blood cells, encompassing all dosage values in-between. Another example would be the selection of a range of from above $8.5 \times 10^8$ to about $2 \times 10^9$, preferably to about $1.2 \times 10^9$, white blood cells, encompassing all dosage values in-between. Another example would be the selection of a range of from above $9 \times 10^8$ to about $2 \times 10^9$, preferably to about $1.2 \times 10^9$, white blood cells, encompassing all dosage values in-between. Another example would be the selection of a range of from above $9.5 \times 10^8$ to about $2 \times 10^9$, preferably to about $1.2 \times 10^9$, white blood cells, encompassing all dosage values in-between. Thus, all dosage ranges that can be selected from the values herein and as would be understood by those of ordinary skill in the art, are encompassed by the present invention.

Methods of measurement of each of the cell populations above mentioned are clearly established in the detail description of the invention.

It is noted that such cell suspension can comprise pharmaceutically acceptable carriers and/or excipients.

In another preferred embodiment of the first aspect of the invention or of any of its preferred embodiments, the lower extremity peripheral artery disease is critical limb ischemia.

In another preferred embodiment of the first aspect of the invention or of any of its preferred embodiments, cells are suspended in a volume of from 5 to 30 ml of a heparinized saline solution, or lactated Ringer solution, preferably comprising about 1% HSA and about 2.5% glucose.

A second aspect of the invention refers to the cell suspension as defined in the first aspect of the invention or of any of its preferred embodiments, for use in a method of treatment of lower extremity peripheral artery disease, preferably critical limb ischemia, via intra-arterial administration, wherein a low pressure blood flow of up to 4 atmospheres is obtained by positioning an inflatable balloon proximal to the occlusive vascular lesion at the distal femoral or popliteal artery and infusing said cell suspension intra-arterially.

A third aspect of the invention refers to one or several pre-filled syringe/s comprising a cell suspension as defined in the first aspect of the invention or of any of its preferred embodiments.

A fourth aspect of the invention refers to the syringe (the pre-filled syringe) as defined in the third aspect of the invention, for use in the treatment or amelioration of lower extremity peripheral artery disease, preferably critical limb ischemia. It is noted that one or more pre-filled syringes can be used per patient.

A fifth aspect of the invention refers to the syringe (the pre-filled syringe) as defined in the third aspect of the invention, for use in a method of treatment of lower extremity peripheral artery disease, preferably critical limb ischemia, via intra-arterial administration, wherein a low pressure blood flow of up to 4 atmospheres is obtained by positioning an inflatable balloon proximal to the occlusive vascular lesion at the distal femoral or popliteal artery and infusing said cell suspension intra-arterially.

In a preferred embodiment of the first to fifth aspects of the invention, the cell suspension or the syringes are provided as a single dose.

In a preferred embodiment of the second and fifth aspects of the invention, the induction of low pressure flow is produced between 1 and 6 minutes and the infusion of said cell suspension is carry-out between 2 and 10 minutes.

A sixth aspect of the invention refers to a manufacturing process of the cell suspension of the invention as defined in the first aspect of the invention or in any of its preferred embodiments, which comprises:

1. Bone marrow (BM) collection is performed by repeated aspirations, preferably from the subject's posterior iliac crest under local or general anesthesia. BM aspirates are then collected, preferably in a transfer bag containing an anticoagulant solution, more preferably a citrate dextrose solution A (ACD-A).
2. The BM is filtered, preferably by gravity, to remove any small bone fragments and to prevent clogging during later steps.
3. The initial BM volume is reduced, preferably to about 50-100 mL, preferably by using the SmartRedux program on the Sepax 2.0 device and associated sterile disposable SmartRedux kit (CS-490.1). This step, which includes plasma and red blood cell (RBC) removal, preferably resulting in about 50-100 mL of buffy coat product, also contributes to the purity of the final product.
4. Optionally, a volume reduction step is performed in one or two cycles dependent on the volume of the starting material to be processed. BM samples with volumes of up to 220 mL are processed in a single cycle and samples of more than 220 mL are processed in two cycles using the same kit. Preferably, for both single and double-cycle volume reduction, the final volume is set to about 50-100 mL.
5. The sterile intermediate sample bag containing volume-reduced BM as established in steps 3 or 4, goes through an automated density gradient centrifugation, followed by two washes of the mononuclear cell (MNC) suspension using a washing solution, preferably composed of 2-4% HSA in saline solution (both pharmaceutical grade). Approximately about 45 mL of BM-MNC product is collected in the output bag and the other components are removed to the waste bag. Preferably, the sterile intermediate sample bag containing volume-reduced BM goes through a NeatCell density gradient centrifugation, followed by two washes of the mononuclear cell (MNC) suspension using a washing solution, preferably composed of 2-4% HSA in saline solution (both pharmaceutical grade). Approximately about 45 mL of BM-MNC product is collected in the output bag and the other components are removed to the waste bag.
6. The BM-MNCs are collected from the product bag, preferably using a 50 mL syringe, and filtered, preferably through a 50 μm filter, preferably into a sterile falcon tube. The product bag is rinsed with wash solution and filtered to improve MNC recovery. The final volume of the BM-MNC drug substance is adjusted to 40-60 mL.

The drug substance is centrifuged and the pellet is re-suspended in the final formulation mix, preferably saline with heparin, or lactated ringer's solution with preferably 1% HSA and preferably 2.5% glucose in a volume of preferably 5-30 ml.

As already stated above, it is noted that the final cell suspension product obtained from the sixth aspect of the invention is dosed based on viable white blood cells, including not only the MNC fraction but also granulocytes. Since the MNCs are the active component, the percentage of MNCs in the final product is considered a quality attribute.

A seventh aspect of the invention refers to the cell suspension product or the product container, preferably one or several syringes, obtained or obtainable by the method of the sixth aspect of the invention. It is noted that such cell suspension product or product container can be used as established in any of the first to fifth aspects of the invention.

DESCRIPTION OF THE INVENTION

Definitions

As used herein "autologous" is understood as referring to a cell preparation where the donor and the recipient are the same individual.

As used herein "allogeneic" is understood as referring to a cell preparation where the donor and the recipient are not the same individual.

As used herein "adult bone marrow derived cells" is understood as a preparation comprising cells, which are not embryonic and are derived from bone marrow obtained from a human donor.

As used herein "cell suspension" is understood as a preparation of cells suspended in a liquid medium.

As used herein "cell suspension of adult bone marrow derived cells" is understood as a preparation of cells, which are not embryonic and are derived from bone marrow obtained from a human donor suspended in a liquid medium.

As used herein "Hematopoietic stem cells which express CD34" is understood as hematopoietic stem cells which express the surface marker CD34 and are identified as CD34 positive by CD34 antibody staining and flow cytometry.

As used herein "Early, non-committed hematopoietic stem cells which express CD34 and do not express CD38" is understood as hematopoietic stem cells which express the surface marker CD34 and are identified as CD34 positive by CD34 antibody staining and flow cytometry, but are identified negative for the surface marker CD38 by CD38 antibody staining and flow cytometry.

As used herein "White blood cells that express CXCR4" is understood as cells which express the surface marker CD45 and CXCR4 and are identified as CD45 and CXCR4 positive by CD45 and CXCR4 antibody staining and flow cytometry. CXCR4 is a receptor for migration factor SDF-1.

As used herein "Stem cells that express CD34 and CXCR4" is understood as cells which express the surface marker CD45, CD34 and CXCR4 and are identified as CD45, CD34 and CXCR4 positive by CD45, CD34 and CXCR4 antibody staining and flow cytometry. CXCR4 is a receptor for migration factor SDF-1.

As used herein "White blood cells that express VEGFR2" is understood as cells which express the surface marker CD45 and VEGFR2 and are identified as CD45 and VEGFR2 positive by CD45 and VEGFR2 antibody staining and flow cytometry. VEGFR2 is a receptor of VEGF, which is a angiogenesis and vasculogenesis.

As used herein "mononuclear cells" is understood as any blood or bone marrow white blood cell (also referred to as leukocytes) having a round nucleus, thereby excluding granulocytes.

As used herein "lower extremity peripheral artery disease" is understood as a narrowing of the arteries other than those that supply the heart or brain. Peripheral artery disease commonly affects the legs, but other arteries may be involved.

As used herein "critical limb ischemia" is understood as sub-division of peripheral artery disease, where the condition is characterized by chronic ischemic at-rest pain, ulcers, or gangrene in one or both legs attributable to objectively proven arterial occlusive disease.

The term "about" in reference to a numeric value means+/−20% of that numeric value. The term "about" in reference to a numeric value also includes+/−10% of that numeric value. The term "about" in reference to a numeric value also includes +/−5% of that numeric value. The term "about" in reference to a numeric value also includes +/−1% of that numeric value.

The terms "comprise" and "comprising" are used in the inclusive, open sense, meaning that additional elements may be included. The term "comprises" also encompasses and may be used interchangeably with the terms "consists of" and "consists essentially of".

As used herein the term "adult" it is meant that the stem cells are not embryonic. In one embodiment, "adult" means post-embryonic or "post-natal". With respect to the stem cells of the present invention, the term "adult stem cell" means that the stem cell is isolated from a tissue or organ of an animal at a stage of growth later than the embryonic stage. Adult stem cells are unlike embryonic stem cells, which are defined by their origin, the inner cell mass of the blastocyst. Adult stem cells according to the invention may be isolated from any non-embryonic tissue, and will include neonates, juveniles, adolescents and adult subjects. Generally, the stem cell of the present invention will be isolated from a non-neonate mammal, and for example from a non-neonate human. Preferably, the stem cells of the present invention are isolated from a human.

The term "isolated" indicates that the cell or cell population to which it refers is not within its natural environment. The cell or cell population has been substantially separated from surrounding tissue.

The marker profile of the new cell suspension product referred to in the present invention can be further defined by the presence and/or absence of additional markers, or by a specific profile of a combination of present and absent markers. In each case, the specific combination of markers may be present as a particular profile within a population of cells and/or a particular profile of markers on individual cells within the population.

The term "marker" as used herein encompasses any biological molecule whose presence, concentration, activity, or phosphorylation state may be detected and used to identify the phenotype of a cell.

Then, cells of the invention are positive for certain phenotypic markers and negative for others. By "positive", it is meant that a marker is expressed within a cell. In order to be considered as being expressed, a marker must be present at a detectable level. By "detectable level" is meant that the marker can be detected using one of the standard laboratory methodologies such as PCR, blotting or flow cytometry analysis as described.

The term "expressed" is used to describe the presence of a marker on the surface of or within a cell. In order to be considered as being expressed, a marker must be present at a detectable level. By "detectable level" is meant that the marker can be detected using one of the standard laboratory methodologies such as PCR, blotting, immunofluorescence, ELISA or FACS analysis. "Expressed" may refer to, but is not limited to, the detectable presence of a protein, phosphorylation state of a protein or an mRNA encoding a protein. A gene is considered to be expressed by a cell of the invention or a cell of the population of the invention if expression can be reasonably detected after 30 PCR cycles, preferably after 37 PCR cycles, which corresponds to an expression level in the cell of at least about 100 copies per cell. The terms "express" and "expression" have corresponding meanings. At an expression level below this threshold, a marker is considered not to be expressed.

DETAILED DESCRIPTION

The Cell Suspension Product

The cell suspension according to the present invention is a product suitable for the treatment or amelioration of lower extremity peripheral artery disease, particularly for the treatment of critical limb ischemia (CLI), more particularly for the treatment of critical limb ischemia (CLI) in patients with DM who have no option for revascularization using surgical bypass or endovascular methods, as an improved therapeutic useful alternative. In this sense, it has been surprisingly found that the cell suspension according to the present invention when used in the treatment or amelioration of lower extremity peripheral artery disease leads to many clinically relevant improvements such as a change in the Rutherford classification from CLI Grade II (category 4) or III (category 5) to Grade I (category 1-3) or Grade 0 (category 0); an improved healing process not only for ulcers but even for major amputations; and an increase in vascular extension and/or vascular density. All the above advantages can be obtained even with a single administration of the cell suspension and are clearly illustrated in example 2.

Generally, the cell suspension of the invention refers to a cell suspension of autologous or allogeneic, preferably autologous, adult bone marrow derived cells, preferably derived from the crest of the ilium (or iliac crest), which comprises:

A. Mononuclear cells (MNC) selected from the list comprising or consisting of:
  i. A population of Lymphocytes;
  ii. A population of Monocytes; and
  iii. A population of Hematopoietic stem cells expressing CD34;
and wherein the cell suspension further comprises:
  B. Granulocytes.

It is noted that the cell populations A) and B) in turn comprise a cell population that expresses CXCR4, a receptor for the migration factor SDF1, from this population it is important to point out the presence of a subpopulation of hematopoietic stem cells expressing CD34 and CXCR4. In addition, the cell populations A) and B) in turn comprise a cell population that expresses VEGFR2, a receptor for angiogenesis factor VEGF that is involved in angiogenesis and vasculogenesis.

Lastly, the cell population A. iii) in turn comprises a cell population that does not express CD38, which are early non-committed hematopoietic stem cells.

Therefore, specifically the suspension according to the present invention is a cell suspension of autologous or allogeneic, preferably autologous, adult bone marrow derived cells comprising: i) hematopoietic stem cells which express CD34; ii) early, non-committed hematopoietic stem cells which express CD34 and do not express CD38; iii) white blood cells that express CXCR4, which is a receptor for migration factor SDF-1; iv) hematopoietic stem cells that express CD34 and CXCR4, which is a receptor for migration factor SDF-1; v) white blood cells that express VEGFR2, which is a receptor for (VEGF) and vi) monocytes, granulocytes and lymphocytes.

It is important to note that the final cell suspension product of the invention is dosed based on viable white blood bone marrow-derived cells, including not only the mononuclear white blood cell fraction (lymphocytes and monocytes and stem cells) but also granulocytes.

Consequently, the cell suspension of the invention refers to autologous or allogeneic, preferably autologous, adult bone marrow derived cells comprising i) hematopoietic stem cells which express CD34 ii) early, non-committed hematopoietic stem cells which express CD34 and do not express CD38; iii) white blood cells that express CXCR4, which is a receptor for migration factor SDF-1, i.e.; iv) hematopoietic stem cells that express CD34 and CXCR4, which is a receptor for migration factor SDF-1, v) white blood cells that express VEGFR2, which is a receptor for vascular endothelial growth factor (VEGF) and vi) monocytes, granulocytes and lymphocytes.

In a preferred embodiment, the cell suspension, in the final formulation which is enriched for mononuclear cells, meaning more than 25% of the white blood cells (WBCs) present in the cell suspension are mononuclear cells, comprises from about $4 \times 10^8$ to about $2 \times 10^8$, autologous or allogeneic white blood bone marrow-derived cells, preferably autologous, preferably derived from the crest of the ilium (or iliac crest), wherein of the total number of from about $4 \times 10^8$ to about $2 \times 10^8$ of white blood cells:
 i. about 20% to about 51% are lymphocytes, and about 3.9% to about 22.3% are monocytes;
 ii. 1.4% to 10% are hematopoietic stem cells that express CD34;
 iii. about 25.3% to about 83.3% of the total number of white blood cells are mononuclear cells;
 iv. about 16.7% to about 74.7% are granulocytes;
 v. about 5.4% to about 38.8% of the total number of white blood cells express CXCR4;
 vi. about 0.07% to about 24.7% of total number of white blood cells express VEGFR2;
 vii. Of the total number of hematopoietic stem cells that express CD34, about 7.7% to about 55.5% are early, non-committed hematopoietic stem cells that do not express CD38 and about 0.7% to about 10.3% are stem cells that express CD34 and CXCR4; and
 viii. The maximum ratio of red blood cells to leucocyte cells is 6.7 and the maximum ratio of platelets to leucocyte cells is 32.

In another preferred embodiment, of the total number of white blood cells 32.3% to 80.0% are mononuclear cells selected from the list consisting of lymphocytes, monocytes and hematopoietic stem cells that express CD34 cells and 20.0% to 67.7%, are granulocytes.

In yet another preferred embodiment, the cell suspension of the invention, in the final formulation, as defined in the precedent paragraph, comprises from about $4 \times 10^8$ to about $1.2 \times 10^9$ white blood cells, more preferably from about $5 \times 10^8$ to about $2 \times 10^9$ white blood cells, still more preferably from about $5 \times 10^8$ to about $1.2 \times 10^9$ white blood cells, and all dosage values between each of the above listed values.

Certain embodiments may be selected as sub-ranges from these values of white blood cells in the final formulation. For example, a specific embodiment may be selected as a white blood cell content of above $8 \times 10^8$ to about $1.2 \times 10^9$ white blood cells. Another example of how a range may be selected in an embodiment would be the selection of a content of about $9 \times 10^8$ to about $1.1 \times 10^9$ white blood cells. A third example of ranges that may be selected for a specific embodiment would be the selection of about $9.5 \times 10^8$ to about $1.05 \times 10^9$ white blood cells. A fourth example of ranges that may be selected for a specific embodiment would be selection of a content such as above $9.8 \times 10^8$ to about $1.02 \times 10^9$ white blood cells.

Other examples of how a range of an embodiment of content or concentration may be selected include a range of from above $6 \times 10^8$ to about $2 \times 10^9$, preferably to about $1.2 \times 10^9$, white blood cells, encompassing all dosage values in-between. Another example would be the selection of a range of from above $7 \times 10^8$ to about $2 \times 10^9$, preferably to about $1.2 \times 10^9$, white blood cells, encompassing all dosage values in-between. Another example would be the selection of a range of from above $8 \times 10^8$ to about $2 \times 10^9$, preferably to about $1.2 \times 10^9$, white blood cells, encompassing all dosage values in-between. Another example would be the selection of a range of from above $8.5 \times 10^8$ to about $2 \times 10^9$, preferably to about $1.2 \times 10^9$, white blood cells, encompassing all dosage values in-between. Another example would be the selection of a range of from above $9 \times 10^8$ to about $2 \times 10^9$, preferably to about $1.2 \times 10^9$, white blood cells, encompassing all dosage values in-between. Another example would be the selection of a range of from above $9.5 \times 10^8$ to about $2 \times 10^9$, preferably to about $1.2 \times 10^9$, white blood cells, encompassing all dosage values in-between. Thus, all dosage ranges that can be selected from the values herein and as would be understood by those of ordinary skill in the art, are encompassed by the present invention.

Methods of measurement of each of the cell populations above mentioned are clearly established in the detail description of the invention. In particular, methods of measurement of each of the lymphocytes, monocytes, granulocytes, platelets and RBCs are conducted using total and differential cell counts with an automated hematology cell counter (ABX Pentra 60, Horiba Medical). Progenitor cell percentages, CXCR4 expressing cell percentages and VEGFR2 expressing cell percentages were determined using a flow cytometer (MACS Quant Analyzer 10, Miltenyi Biotec).

It is noted that such cell suspension can comprise pharmaceutically acceptable carriers and/or excipients.

In another preferred embodiment, the cells of the cell suspension of the invention are suspended in a volume of from 5 to 30 ml of a heparinized saline solution or lactated Ringer solution, preferably comprising about 1% HSA and about 2.5% glucose.

The invention also provides a pharmaceutical composition comprising the cell suspension of the invention as defined above and optionally a pharmaceutically acceptable carrier. The pharmaceutically acceptable carrier can comprise a medium which supports cell viability and functionality. Such medium can be serum-free in order to avoid provoking an immune response in the recipient. The carrier will be buffered and pyrogen free.

Pharmaceutically acceptable carriers and diluents include saline, aqueous buffer solutions, and/or dispersion media. The use of such carriers and diluents is well known in the art. The solution is sterile and of sufficiently low viscosity to allow use of a syringe for administration.

Examples of materials and solutions which can serve as pharmaceutically-acceptable carriers are also well known in the art.

It is noted that in a preferred embodiment the final pharmaceutical formulation solution of the cell suspension product as illustrated in the examples of the present specification was composed of heparinized saline (see table 4). Lactated Ringer solution (2.7 mg/100 mL calcium chloride dihydrate, 320 mg/100 mL sodium lactate, 40 mg/100 mL potassium chloride and 600 mg/100 mL sodium chloride) with the addition of 2.5% glucose and 1% HSA can also be used (see Table 2).

The final formulation medium, as illustrated in the examples of the invention, was prepared fresh for each batch on the day of processing, in the Class A BSC, by adding 10 mL of glucose (2.5%) and 1 mL of HSA (20%) to 9 mL of lactated Ringer's solution.

TABLE 2

| formulation buffer* | | |
|---|---|---|
| Component | Concentration | Grade |
| Ringer solution | | EP, USP for infusion |
| Glucose | 2.5% | EP USP for infusion |
| Human albumin | 1% | EP USP for infusion |
| Saline (0.9% NaCl) | | EP USP for infusion |
| heparin | 20 U/mL | EP USP for infusion |

Abbreviations: EP = European Pharmacopeia; USP = United States Pharmacopeia
*see also Table Therefore, particularly preferred excipients are lactated Ringer solution, preferably with the addition of glucose and HSA.

In another preferred embodiment, the cell suspension of the invention or the pharmaceutical composition of the invention may be frozen in freezing medium. Any medium that preserves the viability of the cells at temperatures between −135° C. and −190° C. is suitable as freezing medium. For example, the freezing medium may comprise 2.5% to 10% DMSO. More specifically, the freezing medium may comprise 5-10% DMSO.

Freezing medium may be based on culture medium or expansion medium described herein, further comprising human serum or any other protein or mix of proteins able to maintain cell integrity after thawing the cells.

After thawing, cells of invention can be washed to remove the DMSO or other freezing medium components before administration or re-suspension in administration solution. Administration solution will be any physiological solution able to be injected in patients without toxicity. Administration solution may comprise 1-15% protein such as human serum albumin.

The pharmaceutical compositions of the invention may also be used in any of the methods of treatment or therapeutic uses described herein.

As already stated, the cell suspension of the present invention accelerates (re)generation of new and existing blood vessels and improves blood flow within existing vessels as illustrated in example 2. Thus, the cell suspension of the invention is especially advantageous in the treatment of lower extremity Peripheral Artery Disease (PAD), preferably CLI, more preferably CLI with DM in patients who have no option for revascularization using surgical bypass or endovascular methods. Example 2 was performed by using a specific drug cell suspension product falling within the definition of the cell suspension of the invention as defined in the first aspect of the invention. Such drug cell suspension product was made of a BM-MNC drug substance formulated in 10-30 mL heparinized saline. Such drug cell suspension product was used in different dosages, preferred dosages were from about $5 \times 10^8$ to about $1 \times 10^9$. The final container used was 1-3 administration syringes. Data on this cell suspension product was collected in the Phase II (study CMMo/ICPD/2008) for 32 subject batches. Table 2 below summarizes the automated cell counter data for each individual subject, including the WBC and differential (lymphocytes, monocytes) counts. Product-related impurities are also listed for each subject, including RBC and platelet concentration, and percentage of granulocytes.

Phenotypic analysis of the same products is also shown in Table 3, which includes an analysis of the following cell types:

| | |
|---|---|
| CD34+ | Hematopoietic stem cells |
| CD34+ CD38− | Early, non-committed HSCs |
| CD133+ | Endothelial progenitor containing cell population |
| CD90+ | Early hematopoietic stem cells |
| CXCR4+ | Cells expressing the SDF-1 receptor |
| VEGFR2+ | Cells expressing vascular endothelial growth factor receptor 2 |
| CD31+ CD146+ CD133− | Mature endothelial cells |
| CD34+ VEGFR2+ CD133+ | Late outgrowth endothelial progenitor cells |
| CD34− CD105+ CD90+ CD73+ | MSCs |

The data collected from the drug substance are shown in Table 2 and Table 3.

TABLE 2

Automated cell count and differential of CMMo/ICPD/2008 drug substance. Data for middle dose ($5 \times 10^8$ WBCs or leukocytes) and high dose ($1.0 \times 10^9$ WBCs or leukocytes) are shown.

| | | | | | patient batch | | | | | | |
|---|---|---|---|---|---|---|---|---|---|---|---|
| | LEU | RBC | PLA | LYMPH | MONO | CD34+ | MNCs | NEU | EOS | BAS | GRA |
| Method | ($\times 10^3$) ACC | ($\times 10^6$) ACC | ($\times 10^3$) ACC | (%) ACC | (%) ACC | (%) PHE | MNC | (%) ACC | (%) ACC | (%) ACC | (%) SUM |
| F01 | 19.59 | 0.05 | 259 | 48.5 | 6.4 | N/A | 45 | 33 | 0.1 | 3.0 | 55.0 |
| F03 | 19.43 | 0.11 | 603 | 42.5 | 12.2 | 1.44 | 45.2 | 33.9 | 0.1 | 1.2 | 54.8 |
| F04 | 20.59 | 0.04 | 69 | 24.1 | 7.2 | 3.77 | 68.6 | 57.7 | 0.1 | 3.1 | 31.4 |
| F05 | 16.87 | 0.04 | 56 | 20.1 | 6.4 | 7.23 | 73.4 | 62 | 0.1 | 2.5 | 26.6 |
| F07 | 8.96 | 0.06 | 242 | 42.2 | 12.6 | N/A | 44.8 | 31.2 | 0.4 | 3.1 | 55.2 |
| F08 | 21.94 | 0.06 | 310 | 36.4 | 7.5 | 3.69 | 56.1 | 42.6 | 0 | 2.7 | 43.9 |
| F09 | 43.29 | 0.06 | 329 | 37.4 | 5.4 | 4.34 | 57.2 | 47.2 | 0 | 4.1 | 42.8 |

TABLE 2-continued

Automated cell count and differential of CMMo/ICPD/2008 drug substance. Data for middle dose (5 × 10⁸ WBCs or leukocytes) and high dose (1.0 × 10⁹ WBCs or leukocytes) are shown.

| | | | | | patient | | | | | | |
|---|---|---|---|---|---|---|---|---|---|---|---|
| | LEU | RBC | PLA | LYMPH | MONO | CD34+ batch | MNCs | NEU | EOS | BAS | GRA |
| Method | (×10³) ACC | (×10⁶) ACC | (×10³) ACC | (%) ACC | (%) ACC | (%) PHE | MNC | (%) ACC | (%) ACC | (%) ACC | (%) SUM |
| F10 | 8.75 | 0.04 | 277 | 45.1 | 22.1 | 2.54 | 32.7 | 25.3 | 0.1 | 2.3 | 67.3 |
| F11 | 17.28 | 0.02 | 38 | 28.1 | 7.0 | 10.05 | 64.8 | 54 | 0.1 | 4.9 | 35.2 |
| F14 | 30.74 | 0.07 | 232 | 47.4 | 10.5 | 4.20 | 42.1 | 27.3 | 0 | 7.1 | 57.9 |
| F15 | 23.12 | 0.06 | 280 | 47.1 | 11.1 | 6.50 | 41.7 | 30.4 | 0.1 | 4.2 | 58.3 |
| F16 | 14.39 | 0.04 | 153 | 26.6 | 11 | 4.75 | 62.3 | 51.2 | 0.1 | 4.6 | 37.7 |
| F17 | 25.31 | 0.06 | 235 | 36.2 | 6.7 | 3.68 | 57.1 | 49 | 0 | 2.3 | 42.9 |
| F18 | 22.89 | 0.07 | 191 | 30.2 | 8.2 | 3.00 | 61.6 | 48.9 | 0 | 3.3 | 38.4 |
| F20 | 16.46 | 0.06 | 229 | 51.1 | 11.2 | N/A | 37.7 | 21.8 | 0 | 4.1 | 62.3 |
| F21 | 31.55 | 0.05 | 153 | 48.2 | 9.4 | 2.20 | 42.2 | 32.5 | 0.2 | 2.9 | 57.8 |
| F22 | 10.46 | 0.05 | 157 | 42.0 | 17.4 | 1.67 | 40.5 | 31.1 | 0.1 | 3.4 | 59.5 |
| F23 | 18.36 | 0.03 | 144 | 40.2 | 6.2 | 3.30 | 53.5 | 42.9 | 0.1 | 2.9 | 46.5 |
| F25 | 27.86 | 0.06 | 239 | 36.5 | 6.0 | 3.30 | 57.5 | 51.7 | 0 | 6.4 | 42.5 |
| F26 | 25.83 | 0.08 | 337 | 43.0 | 14.3 | 4.28 | 42.7 | 28.4 | 0 | 2.8 | 57.3 |
| F27 | 23.8 | 0.06 | 538 | 38.1 | 7.0 | 2.06 | 54.9 | 39.9 | 0 | 3.2 | 45.1 |
| F28 | 19.56 | 0.04 | 93 | 46.4 | 5.9 | 3.67 | 47.7 | 33.5 | 0 | 2.2 | 52.3 |
| F30 | 20.74 | 0.09 | 246 | 45.4 | 7.7 | 2.19 | 46.9 | 31.7 | 0 | 4.1 | 53.1 |
| F31 | 15.67 | 0.06 | 230 | 41.6 | 14.6 | 4.68 | 43.7 | 32.2 | 0.1 | 4.8 | 56.3 |
| F32 | 26.34 | 0.15 | 489 | 50.6 | 16.9 | 5.40 | 32.3 | 17.5 | 0.2 | 4.5 | 67.7 |
| F33 | 35.3 | 0.1 | 370 | 40.7 | 3.9 | 3.59 | 55.4 | 44.7 | 0 | 4.7 | 44.6 |
| F34 | 56.97 | 0.11 | 398 | 26.5 | 5.7 | 2.73 | 67.8 | 56.1 | 0 | 5.1 | 32.2 |
| F35 | 28.94 | 0.05 | 107 | 25.6 | 6.4 | 9.24 | 67.8 | 60.5 | 0.2 | 3.2 | 32.2 |
| F37 | 19.71 | 0.04 | 201 | 26.7 | 10.7 | 3.92 | 62.5 | 51.2 | 0.1 | 3.6 | 37.5 |
| F38 | 29.41 | 0.07 | 504 | 30.0 | 20.8 | 4.12 | 49.1 | 39.5 | 0.1 | 2.7 | 50.9 |
| F39 | 26.03 | 0.03 | 174 | 31.7 | 22.3 | 4.44 | 45.9 | 40.6 | 0.1 | 3.6 | 54.1 |
| F40 | 24.72 | 0.07 | 304 | N/M | 19.9 | 3.18 | 80 | 48.9 | 0.1 | 2.7 | 20.0 |
| Min. | 8.75 | 0.02 | 38 | 20.1 | 3.9 | 1.44 | 32.3 | 17.5 | 0 | 1.2 | 20.0 |
| Max | 56.97 | 0.15 | 603 | 51.1 | 22.3 | 10.05 | 80.0 | 62.0 | 0.4 | 7.1 | 67.7 |

Methods used:
ACC = drug substance composition assessed using automated cell counter (ABX Pentra 60);
PHE = phenotypic analysis of drug substance (MACS Quant Analyzer 10, Miltenyi Biotec);
MNC = calculated as proportion of white blood cells not granulocytes;
SUM = calculated from constitute cell counts.
Abbreviations:
LEU = leukocyte;
RBC = red blood cell;
PLT = platelet;
LYMPH = lymphocyte;
MONO = monocyte;
CD34+ = cells expressing CD34;
MNCs = mononuclear cells;
NEU = neutrophil;
BAS = basophil;
EOS = eosinophil;
GRA = granulocytes;
N/A = not available;
N/M = not meaningful.

TABLE 3

Phenotypic analysis of CMMo/ICPD/2008 drug substance. Data collected in the Phase II (study CMMo/ICPD/2008) for 32 subject.

| patient batch Method | CD34+ (%) PHE | CD34+/CD38− (%) PHE | CXCR4+ (%) PHE | CD34+/CXCR4 (%) PHE | VEGFR2+ (%) PHE |
|---|---|---|---|---|---|
| F01 | N/A | | | | |
| F03 | 1.44 | 18.05 | 15.10 | 0.69 | 24.73 |
| F04 | 3.77 | 26.25 | 5.38 | 1.06 | 2.23 |
| F05 | 7.23 | 7.74 | 18.63 | 1.10 | 0.30 |
| F07 | N/A | N/A | N/A | N/A | N/A |
| F08 | 3.69 | 14.9 | 22.59 | 9.48 | 0.25 |
| F09 | 4.34 | 22.11 | 31.93 | 9.44 | 0.19 |
| F10 | 2.54 | 20.47 | 32.00 | 2.75 | 0.25 |
| F11 | 10.05 | 25.77 | 31.56 | 4.87 | 0.40 |

TABLE 3-continued

Phenotypic analysis of CMMo/ICPD/2008 drug substance. Data collected in the Phase II (study CMMo/ICPD/2008) for 32 subject.

| patient batch Method | CD34+ (%) PHE | CD34+/CD38− (%) PHE | CXCR4+ (%) PHE | CD34+/CXCR4 (%) PHE | VEGFR2+ (%) PHE |
|---|---|---|---|---|---|
| F14 | 4.20 | 18.33 | 20.27 | 6.66 | 0.30 |
| F15 | 6.50 | 41.84 | 21.93 | 0.92 | 0.53 |
| F16 | 4.75 | 22.1 | 38.79 | 4.00 | 0.28 |
| F17 | 3.68 | 28.53 | 25.62 | 5.43 | 0.76 |
| F18 | 3.00 | 34 | 21.10 | 3.33 | 0.07 |
| F20 | N/A | N/A | N/A | N/A | N/A |
| F21 | 2.20 | 55.45 | 11.20 | 6.81 | 0.13 |
| F22 | 1.67 | 19.16 | 16.00 | 3.59 | 0.64 |
| F23 | 3.30 | 10.00 | 27.10 | 10.3 | 0.47 |
| F25 | 3.30 | 18.48 | 20.05 | 3.33 | 0.36 |
| F26 | 4.28 | 21.26 | 26.66 | 5.84 | 0.65 |
| F27 | 2.06 | 17.47 | 23.79 | 1.45 | 0.21 |
| F28 | 3.67 | 18.52 | 14.55 | 5.17 | 0.56 |
| F30 | 2.19 | 23.74 | 29.44 | 10.04 | 0.33 |
| F31 | 4.68 | 42.73 | 32.06 | 9.61 | 0.66 |
| F32 | 5.40 | 24.07 | 22.88 | 5.37 | 0.45 |
| F33 | 3.59 | 11.14 | 15.62 | 1.94 | 0.37 |
| F34 | 2.73 | 34.43 | 7.69 | 1.83 | 0.46 |
| F35 | 9.24 | 20.23 | 21.53 | 2.59 | 1.07 |
| F37 | 3.92 | 33.92 | 35.21 | 4.84 | 0.65 |
| F38 | 4.12 | 35.92 | 30.42 | 2.66 | 1.78 |
| F39 | 4.44 | 18.01 | 27.51 | 1.80 | 0.99 |
| F40 | 3.18 | 30.50 | 15.88 | 2.83 | 1.37 |
| Min. | 1.44 | 7.74 | 5.38 | 0.69 | 0.07 |
| Max | 10.05 | 55.45 | 38.8 | 10.3 | 24.7 |

Methods used: PHE = phenotypic analysis of drug substance (MACS Quant Analyzer 10, Miltenyi Biotec); Abbreviations: CD34+ = hematopoietic stem cells expressing CD34; CD34+/CD38− = proportion of hematopoietic stem cells expressing CD34 that do not express CD38; CD45+/CXCR4+ = proportion of leukocytes that express CD45 and also express CXCR4; CD34+/CXCR4 = proportion of hematopoietic stem cells expressing CD34 that also express CXCR4; CD45+/VEGF+ = proportion white blood cells expressing VEGF; N/A = not available. All cells also express CD45.

Based on the results collected in the Phase II (study CMMo/ICPD/2008) for 32 subject batches illustrated in tables 2 and 3 above, we have provided the characterization of the cell suspension product of the present invention.

It is noted that the present invention further encompasses 1-3 (pre-filled) syringes comprising the cell suspension of the invention.

In addition, if desired, the cells of the cell suspension of the invention of the invention can be modified genetically by any conventional method including, by way of illustration but non-limiting, processes of transgenesis, deletions or insertions in their genome, etc.

Manufacturing Process of the Cell Suspension Product

The cell suspension product of the invention can be manufactured in a number of ways, however, they are preferably manufactured as detailed in example 1 so that the cell suspension of the invention can be considered to be a minimally manipulated BM-MNC (bone marrow-mononuclear cell) product, because the manufacturing process consists only of density, particle size and gravity-based separation steps intended to enrich the MNC fraction in the BM aspirate, by removal of plasma, platelets, RBCs and granulocytes.

The manufacturing process as described in example 1 is briefly summarized as follows:

Step 0. Bone marrow (BM) collection is performed by repeated aspirations, preferably from the subject's posterior iliac crest under local anesthesia. BM aspirates are then collected, preferably in a transfer bag containing anticoagulant citrate dextrose solution A (ACD-A) anticoagulant.

Step 1: Filtration—The BM is filtered, preferably by gravity, to remove any small bone fragments and to prevent clogging during later steps.

Step 2: SmartRedux volume reduction—The initial BM volume is reduced to about 50-100 mL, preferably by using the SmartRedux program on the Sepax 2.0 device and associated sterile disposable SmartRedux kit (CS-490.1), following manufacturer's instructions. This step, which includes plasma and red blood cell (RBC) removal, resulting in about 50-100 mL of buffy coat product, also contributes to the purity of the final product.

The volume reduction step is performed one or two times dependent on the volume of the starting material to be processed. BM samples with volumes of up to 220 mL are processed in a single cycle and samples of more than 220 mL are processed in two cycles using the same kit.

For both single and double-cycle volume reduction, the final volume is set to about 50-100 mL.

Steps 3-4: NeatCell density gradient—The sterile intermediate sample bag containing volume-reduced BM goes through a density gradient centrifugation, followed by two washes of the mononuclear cell (MNC) suspension using a washing solution, preferably composed of 2-4% HSA in saline solution (both pharmaceutical grade). Approximately about 45 mL of BM-MNC product is collected in the output bag and the other components are removed to the waste bag.

Step 5: BM-MNC filtration—The BM-MNCs are collected from the product bag using a 50 mL syringe and filtered through a 50 μm filter into a sterile falcon tube. The product bag is rinsed with wash solution and filtered to improve MNC recovery. The final volume of the BM-MNC drug substance is adjusted to 40-60 mL.

A final step (step 6) consists on the preparation of the final cell suspension product of the invention. Such final product is dosed based on viable white blood cells, including not only the MNC fraction but also granulocytes. Since the MNCs are the active component, the percentage of MNCs in the final product is considered a quality attribute. In this sense, there are some process parameters that can affect the quality attributes of the final product. In this regard, steps that can affect the percentage of MNCs in the final product considered important in the manufacturing of the product, are shown in table 5.

TABLE 5

Steps and parameters associated to the manufacturing process

| Step | Parameter | Criticality |
|---|---|---|
| Filtration | Size | Presence of bone pieces may interfere with purification efficiency and may interfere with the administration procedure |
| SmartRedux | Centrifugation: speed and duration | This gravity based separation step contributes directly to the purity of the final product. Therefore, the parameter settings required to establish the separation are critical. |
| NeatCell | Ficoll density | Determines the cell populations that will be purified. The density used is 1.077 gr/ml |
| | Ficoll volume | Affects MNC recovery |
| | Ficoll centrifugation speed and duration | Affects MNC recovery |
| | Wash centrifugation speed and duration | Affects MNC recovery |

Abbreviations: MNC = mononuclear cells

SmartRedux step—this step is intended to reduce the initial BM volume to a volume small enough to be processed in the Neatcell procedure (NeatCell has a maximum input volume of 120 mL). In addition, the SmartRedux step includes fractionation into RBCs, plasma and buffy coat product, which contributes to the purity of the NeatCell product.

Important parameters related to this step are the centrifugation speed and duration, as these parameters will directly affect the recovery of MNCs from the BM aspirate.

NeatCell step—The automated MNC enrichment method used is designed and standardized by the manufacturer, intended to enrich a BM aspirate for MNCs and is therefore important. The Hct of the NeatCell starting material is an important material attribute, because it affects the efficiency of MNC purification. Important process parameters are fixed in the NeatCell program, including centrifugation speed and duration, and Ficoll density and volume.

Within the MNC compartment, multiple cell populations are thought to play important roles in the mode of action of the final product. Hence, presence and functionality of these cells are considered quality attributes (CQAs).

The MNC fraction obtained after Ficoll density gradient centrifugation contains those cells that have a lower density than the Ficoll and are therefore not dense enough to penetrate into the Ficoll layer during centrifugation. Consequently, the density of the Ficoll used in the process directly affects the composition of the MNC population and is therefore considered an important process parameter. The density used is 1.077 gr/ml.

Manufacturing is a continuous process, and does not involve any activation steps or other extensive manipulations of cells that may affect functionality of the specific cell populations within the MNC fraction. Process duration may affect functionality of cells and therefore, no hold times are incorporated in the process and the entire process is preferably completed within 4-5 hours in a clean room environment. Functionality may also be affected by the subject disease status and general subject physiological variability.

Based on the above, a further aspect of the invention refers to a manufacturing process of the cell suspension of the invention, which comprises:

1. Bone marrow (BM) collection is performed by repeated aspirations, preferably from the subjects' posterior iliac crest under local or general anesthesia. BM aspirates are then collected, preferably in a transfer bag containing an anticoagulant solution, more preferably a citrate dextrose solution A (ACD-A).
2. The BM is filtered, preferably by gravity, to remove any small bone fragments and to prevent clogging during later steps.
3. The initial BM volume is reduced, preferably to about 50-100 mL, preferably by using the SmartRedux program on the Sepax 2.0 device and associated sterile disposable SmartRedux kit (CS-490.1). This step, which includes plasma and red blood cell (RBC) removal, preferably resulting in about 50-100 mL of buffy coat product, also contributes to the purity of the final product.
4. Optionally, the volume reduction step is performed in one or two cycles dependent on the volume of the starting material to be processed. BM samples with volumes of up to 220 mL are processed in a single cycle and samples of more than 220 mL are processed in two cycles using the same kit. Preferably, for both single and double-cycle volume reduction, the final volume is set to about 50-100 mL.
5. The sterile intermediate sample bag containing volume-reduced BM as established in steps 3 or 4, goes through a density gradient centrifugation, followed by two washes of the mononuclear cell (MNC) suspension using a washing solution, preferably composed of 2-4% HSA in saline solution (both pharmaceutical grade). Approximately about 45 mL of BM-MNC product is collected in the output bag and the other components are removed to the waste bag. More preferably, the sterile intermediate sample bag containing volume-reduced BM goes through a NeatCell density gradient centrifugation, followed by two washes of the mononuclear cell (MNC) suspension using a washing solution, preferably composed of 2-4% HSA in saline solution (both pharmaceutical grade). Approximately about 45 mL of BM-MNC product is collected in the output bag and the other components are removed to the waste bag.
6. The BM-MNCs are collected from the product bag, preferably using a 50 mL syringe, and filtered, preferably through a 50 μm filter, into a sterile falcon tube. The product bag is rinsed with wash solution and filtered to improve MNC recovery. The final volume of the BM-MNC drug substance is adjusted to 40-60 mL.

It is also important to note that the manufacturing of the cell suspension of the invention is preferably a continuous process involving the enrichment of mononuclear cells, wherein the process does not include the option of reprocessing.

Following preparation of the drug substance, centrifugation of MNCs is preferably performed at 760×g for 10 mins at room temperature. The cells are re-suspended in the final formulation (preferably heparinized saline or lactated Ringer's solution supplemented with 2.5% glucose and 1% HSA and transferred to sterile non-pyrogenic plastic syringe(s) under sterile conditions).

Of the final product, 2-3 mL can be optionally transferred into a vial for quality control (QC) testing and preferably 8 to 12 mL is transferred into each sterile non-pyrogenic plastic syringe under sterile conditions. The syringe, with a closed cone to prevent contamination, is then packaged in a sterile single-use plastic zipper bag and a transportation box for transportation to the participating interventional radiology unit for administration to the subject.

An overview of the manufacturing process is shown in the figures.

Applicability of the Cell Suspension Product

Results clearly illustrated in example 2 showed that within the first 12 months following the administration of cell suspension of the invention, subjects achieved a clinically relevant response as demonstrated by a reduction in their classification to Rutherford Category 1-3 (grade 1) (29 (64%) subjects), which compared favorably to the control group, in which only 2 (13%) subjects responded.

At the Baseline Visit, 25 (56%) subjects in the treatment group who received an infusion of the cell suspension of the invention presented with non-healing ischemic ulcers, but by the Month 12 post-administration follow-up visit, 18 (75%) subjects no longer had ulcers present (one major amputation) with 24 (60%) subjects showing an increase in TcPO2≥40 mmHg, which is a reliable prediction of healing. Vasculogenesis was assessed at Month 6 post-administration of the cell suspension of the invention. In subjects treated with the cell suspension of the invention, vasculogenesis was present in 26 (62%) subjects: 7, 8, and 9 subjects in the lowest, middle, highest groups, respectively.

No subject experienced a Suspected Unexpected Serious Adverse Reaction (SUSAR) during the treatment of during follow-up. Three AEs were considered to be related to the route of administration and were minor injection site reactions. No subject discontinued the trial prematurely as a result of an AE and no subjects experienced an AE related to the cell suspension of the invention. No SAEs occurred prior to administration of Rexmyelocel-T and no SAE occurred during the first 24 hours after administration of Rexmyelocel-T. A total of 41 SAEs were recorded by 23 subjects during the follow-up period (12 months), 17 SAEs (nine subjects) in the control group and 24 SAEs (14 subjects) in the Rexmyelocel-T treatment groups: lower dose $1\times10^8$ BM-MNCs: four subjects; middle dose $5\times10^8$ BM-MNCs: four subjects; highest dose $1\times10^9$ BM-MNCs: six subjects. Two subjects died as a result of cardiovascular disease.

Therefore, it is thus clear that the cell suspension of the invention is especially advantageous in the treatment of lower extremity Peripheral Artery Disease (PAD), preferably CLI, more preferably CLI with DM in patients who have no option for revascularization using surgical bypass or endovascular methods.

Hence, a further aspect of the invention refers to the cell suspension, the pre-filled syringe or the pharmaceutical composition as defined in the section entitled "THE CELL SUSPENSION PRODUCT" is use in the treatment or amelioration of lower extremity peripheral artery disease, preferably in a human subject.

Preferably, the lower extremity peripheral artery disease is critical limb ischemia.

More preferably, the cell suspension, the pre-filled syringe or the pharmaceutical composition as defined in the section entitled "THE CELL SUSPENSION PRODUCT", is use in a method of treatment of lower extremity peripheral artery disease, preferably critical limb ischemia, via intra-arterial administration, wherein a low pressure blood flow of up to 4 atmospheres is obtained by positioning an inflatable balloon proximal to the occlusive vascular lesion at the distal femoral or popliteal artery and infusing said cell suspension intra-arterially.

EXAMPLES

Example 1. Materials and Methods

1. Cell Suspension and Method of Production Thereof.

To illustrate the present invention, a cell suspension according to the present invention has been used in the following examples made of an autologous cell suspension of BM-MNCs composed of several mature cell types as well as hematopoietic progenitor cells. The formulation of the final product was based on the number of viable WBCs present.

Characterization of the cell suspension of the invention was conducted using total and differential cell counts with an automated hematology cell counter (ABX Pentra 60, Horiba Medical). Progenitor cell percentages and WBCs (CD45+ cells) expressing migration factor SDF-1 receptor CXCR4 or WBCs expressing angiogenesis factor VEGF receptor 2 were determined using a flow cytometer (MACS Quant Analyzer 10, Miltenyi Biotec).

The concentration of white blood cells (WBCs), the proportion of lymphocytes, monocytes, granulocytes and progenitor cells and total WBCs expressing CXCR4 or VEGFR2 from 32 clinical batches are presented in Table 6.

TABLE 6

Cell composition from 32 clinical batches from CMMo/ICPD/2008

| Cell type | Technique/cell surface marker | Cell count/ratio |
| --- | --- | --- |
| Leucocytes (white blood cells) | ACC | $1 \times 10^8$-$1 \times 10^9$ |
| Red blood cells/white blood cells | Ratio | 1.15-6.7x |
| Platelet/white blood cells | Ratio | 2.2-31.7x |
| Neutrophils | ACC | $2.5 \times 10^7$-$5.6 \times 10^8$ |
| Lymphocytes | ACC | $2.4 \times 10^7$-$5.1 \times 10^8$ |
| Monocytes | ACC | $6.4 \times 10^6$-$2.0 \times 10^8$ |
| Eosinophils | ACC | 0-$7.1 \times 10^7$ |
| Basophils | ACC | $1.2 \times 10^6$-$7.1 \times 10^7$ |
| Granulocytes | ACC | $2.8 \times 10^7$-$6.1 \times 10^8$ |
| Mononuclear cells | WBC-granulocytes | $3.6 \times 10^7$-$7.8 \times 10^8$ |
| Hematopoietic stem cells | Flow cytometry CD34+ | $1.4 \times 10^6$-$5.4 \times 10^7$ |
| Cells expressing CXCR4, which is a receptor for SDF-1 migration marker | Flow cytometry CXCR4+ | $5.4 \times 10^6$-$3.2 \times 10^8$ |
| Stem cells expressing CXCR4, which is a receptor for SDF-1 migration marker | Flow cytometry CD34+/CXCR4+ | $1.0 \times 10^4$-$4.1 \times 10^6$ |
| Cells expressing receptor VEGFR2 for angiogenesis factor VEGF | Flow cytometry VEGFR2 | $7.0 \times 10^4$-$2.5 \times 10^7$ |

Abbreviations: ACC = automated cell counter, WBC = white blood cells.
Data presented as minimum to maximum.

The cell suspension of the invention was manufactured under GMP conditions. All process steps were performed in a class B clean room, where semi-closed manipulations (spike connection and luer lock connections) and open manipulations were performed in a Class A BSC.

In brief, bone marrow was filtered aseptically to remove bone pieces, followed by an automated volume reduction step to obtain a volume small enough to be processed further.

Next, cells were subjected to automated Ficoll density gradient centrifugation, including wash steps. The product was filtered resulting in a 50 mL BM-MNCs fraction, which was the drug substance.

The entire drug substance manufacturing process was closed, except for spike and luer lock connections. Cell separation steps were performed in an automated system to ensure standardization of the process.

A flow diagram of the manufacturing process of the cell suspension of the invention is provided in FIG. 1. In addition, the manufacturing process is described in detail below:

Step 0: Bone marrow (BM) collection was performed by repeated aspirations from the subject's posterior iliac crest under local anesthesia, using 5 mL syringes coupled to a BM aspirator. BM aspirates were collected in a 600 mL transfer bag containing anticoagulant citrate dextrose solution A (A ACD-A) anticoagulant, until a volume of approximately 250-350 mL is reached. The transfer bag containing fresh BM is packaged according to instructions, and prepared for shipment. BM is shipped at room temperature (15-21° C.) to Rexgenero in a single shipment for immediate processing Step 1: Filtration—The BM was filtered by gravity through a 200 µm inline filter to remove any small bone fragments and to prevent clogging during later steps. After filtration, a sample was collected for in-process tests and the collection bag was weighed, with the mass converted to volume, which provides the input volume in the settings for cell processing.

Step 2: SmartRedux volume reduction—The initial BM volume of approximately 300 mL was reduced to 50 mL using the SmartRedux program on the Sepax 2.0 device and associated sterile disposable SmartRedux kit (CS-490.1), following manufacturer's instructions. This step, which includes plasma and red blood cell (RBC) removal, resulting in 50 mL of buffy coat product, also contributes to the purity of the final product. The volume reduction step was performed one or two times dependent on the volume of the starting material to be processed. BM samples with volumes of up to 220 mL were processed in a single cycle and samples of more than 220 mL were processed in two cycles using the same kit. For both single and double-cycle volume reduction, the final volume was set to 50 mL.

Steps 3-4: NeatCell density gradient—The sterile intermediate sample bag containing volume-reduced BM was connected to the Neatcell kit (CS-900.2) and processed using the NeatCell program on the Sepax 2.0 device, following manufacturer's instructions. This step consisted of a density gradient centrifugation on Ficoll 1077, followed by two washes of the mononuclear cell (MNC) suspension using a washing solution composed of 2.5% or 4% HSA in saline solution (both pharmaceutical grade). Approximately 45 mL of BM-MNC product was collected in the output bag and the other components were removed to the waste bag.

Steps 5: BM-MNC filtration—The BM-MNCs were collected from the product bag using a 50 mL syringe and filtered through a 50 µm filter into a sterile falcon tube. The product bag was rinsed with wash solution and filtered to improve MNC recovery. The final volume of the BM-MNC drug substance was adjusted to 50 mL.

2. Selection of Study Population

A total 60 subjects with CLI Rutherford grade II (Category 4) or grade III (Category 5) and DM, who were unable to undergo surgical or endovascular revascularization (50 males (83%) and 10 females (17%)) with an average age of 64.3 (±9.5) (range: 46-80 years) were enrolled and randomly assigned in a 1:1:1:1 ratio to receive a single administration of the cell suspension of the invention (at one of three dose levels; $1\times10^8$, $5\times10^8$ or $1\times10^9$ BM-MNCs; 15 subjects per treatment group) in addition to standard-of-care or to be treated according to standard-of-care alone (15 subjects). The cell suspension of the invention was administered intra-arterially in a single infusion. For this trial, stratified randomization was applied and strata were constructed for Rutherford CLI Grade II and III (Categories 4 and 5) with no option for endovascular or surgical revascularization according to the Transatlantic Inter-Society Consensus Document on Management of Peripheral Arterial Disease (TASC II). In the event that CLI was present in both legs, the infusion was administered to the leg determined by the Investigator to have the more advanced/severe disease provided that the leg has not already had surgical amputation of the toes or above. Trial subjects were assessed at the Baseline Visit (Visit 1), at 24 hours and Months 1, 3, 6, 9, 12 post-administration of Rexmyelocel-T (Visits 3, 4, 5, 6, 7, and 8 respectively). Subjects assigned to the control group were not required to show up for Visits 2 and 3.

3. Inclusion Criteria

Subjects were eligible for trial inclusion if they met all of the following inclusion criteria:
 1. Subjects of both sexes aged 18 and 80 years.
 2. Subjects receiving treatment for Type I or Type II DM.
 3. CLI Grade II and III (Category 4 and 5) according to Rutherford.
 4. Inability to surgical or endovascular revascularization as recommended by the TASC II.
 5. Life expectancy>two years.
 6. No major amputation is expected in the limb to be treated in the next 12 months after inclusion.
 7. Normal biochemical parameters, defined by: leukocytes≥3000/mL, neutrophils≥1500/mL, platelets≥100000/mm3, AST/ALT≤2.5× standard range, creatinine≤2.5 mg/dL
 8. Subjects provided written informed consent for participation in the trial.
 9. Women of childbearing potential must have negative results on a pregnancy test following standard procedures of each hospital performed at the time of inclusion in the trial and commit to using a medically approved birth control during the trial.

4. Exclusion Criteria

Subjects were excluded from trial participation if they met any of the following exclusion criteria:
 1. History of neoplasia or hematologic disease (myeloproliferative disease, leukemia or myelodysplastic syndrome).
 2. Subjects with uncontrolled hypertension (defined as blood pressure>180 mmHg/110 mmHg on more than one occasion).
 3. Severe heart failure (New York Heart Association Stage IV).
 4. Subjects with malignant ventricular arrhythmias, or unstable angina.
 5. Diagnosis of deep vein thrombosis in the three months before screening.

6. Active infection or gangrene present on the same day the administration of Rexmyelocel-T is planned.
7. Concomitant therapies including hyperbaric oxygen therapy, vasoactive substances, Cox-II inhibitors.
8. BMI>40 kg/m$^2$.
9. Subjects with a diagnosis of alcoholism at the time of inclusion.
10. Proliferative retinopathy.
11. Concomitant disease that reduced life expectancy to <one year.
12. HIV infection, Hepatitis B or Hepatitis C.
13. Subjects who were unwilling or unable to comply with all aspects of the protocol.
14. Heart failure or ejection fraction<30%.
15. Stroke or myocardial infarction in the three months before the screening visit.
16. Anemia (hemoglobin<10 g/dL).
17. Leukopenia.
18. Thrombocytopenia (<100,000 platelets/mm$^3$).
19. Pregnant women or women of childbearing age who did not use adequate contraception.
20. Subjects who participated in a clinical trial within the three months before screening for this trial.

5. Removal of Subjects from the Study

Subjects could be removed from the trial for any of the following reasons:

Failure to achieve optimal final concentration of the cell suspension based on the result at randomization. In this case, the PI should decide whether the product would be administered.

Presence of a serious adverse event (SAE) between informed consent to the planned administration date.

Major protocol deviation. The discovery post-randomization that the subject failed to meet protocol entry criteria or did not adhere to protocol requirements, and continued participation posed an unacceptable risk to the subjects' health.

The subject experienced an AE or pre-treatment event that required early termination because continued participation imposed an unacceptable risk to the subject's health or the subject was unwilling to continue because of the AE or pretreatment event.

Voluntary withdrawal. The subject (or the subject's legally acceptable representative) wished to withdraw from the trial.

Lost to follow-up. The subject did not return to the clinical and attempts to contact the subject were unsuccessful. Attempts to contact the subject were documented. If a subject withdrew from the trial all procedures scheduled for the Early Termination visit were performed, if possible.

According to good clinical practice, all subjects who withdrew from the trial prematurely were recommended an alternative treatment. If the withdrawal was due to the occurrence of a significant AE (adverse effects), the subject was to be monitored by the Investigator to completion, i.e., until the AE resolved or until it was determined to be a permanent event. The primary reason for trial discontinuation was recorded on the CRF.

6. Treatments Administered

Investigational Product

Under local anesthesia and sedation, a volume of BM (90-420 mL) was harvested by successive aspirations from the iliac crest. The BM was collected in a transfer bag containing ACD-A solution as an anticoagulant in a ratio of 1:5 BM volume (see point 1 above)

A suspension of BM-MNCs was obtained by density gradient centrifugation, without modification or addition of any product likely to affect its biological functionality.

The cell suspension of the invention was administered at single doses of:

1×10$^8$ BM-MNCs.
5×10$^8$ BM-MNCs.
1×10$^9$ BM-MNCs.

The cell suspension of the invention was administered using an intra-arterial catheter. Target limb arteries were cannulated through a trans-femoral approach with an over-the-wire catheter balloon (adapted to the popliteal diameter) that was advanced as distally as possible but in all cases below the knee and positioned proximal to the occlusive vascular lesions, usually at the distal femoral or popliteal artery. At this point, the balloon was inflated to block blood flow and the cell suspension of the invention was slowly infused for three minutes (min). After administration, the balloon was deflated and ante-grade blood flow restored.

The administration of the cell suspension of the invention was performed between three and five hours after BM collection by a vascular specialist (interventional radiologist or vascular surgeon) delivered directly from the cell therapy unit.

All subjects were treated with the current standard-of-care for infra-popliteal severe atherosclerotic vascular disease, as described by the TASC II treatment guidelines.

7. Change in Rutherford Classification

Critical limb ischemia includes patients with lower extremity rest pain, ischemic ulcers or gangrene secondary to severely compromised blood flow in the affected limb persisting for more than two weeks. PAD classification of subjects was conducted throughout the trial by vascular specialists using Rutherford Grades rather than Categories because a standard treadmill exercise test was not performed and it was therefore not possible to formally distinguish between mild, moderate or severe IC.

IC (Grade I, Categories 1-3) was defined as extremity muscle pain, discomfort, or weakness that is induced by exercise (produced by walking or muscular activity) and is promptly relieved by cessation of the activity unlike pain at rest which is continuous in patients with CLI.

Rutherford Grade 0 was used to identify those subjects, who had no symptoms, or merely had a sensation of coldness or had no clinical signs of occlusive disease, or a modest pulse diminution.

A non-healing ischemic ulcer implies that there is insufficient arterial perfusion in the lower limb to support the inflammatory response required for healing. Associated with this, there is usually ischemic rest pain and objective evidence of diffuse pedal ischemia (CLI Rutherford Grade Categories 5-6).

Ischemic rest pain indicates diffuse pedal ischemia, (Grade II-IV, Categories 4-6) and cannot readily be controlled by analgesics. The pain is localized in the forefoot and toes or in the vicinity of focal ischemic lesions. It is made worse by elevating the limb. Diffuse pedal ischemia with ischemic rest pain is commonly associated with ankle pressure<40 mmHg and ABI<0.8.

The subjects were classified based on the presence of ischemic rest pain (with or without non-healing ischemic ulcers), ischemic muscle pain induced by exercise (IC), or asymptotic disease. To classify trial subjects, the clinical symptoms were combined with objective evidence of diffuse pedal ischemia through measuring the ABI (if this could be reliably assessed.

The change in Rutherford classification from baseline to Months 1, 3, 6, 9 and 12 was assessed.

A clinical improvement was defined as a single Rutherford Grade (Category) improvement from baseline. A clinically relevant improvement was defined as change in Rutherford classification from CLI Category 4 or 5 to IC Category 3 or lower, at 3, 6, 9, or 12 months after the administration of Rexmyelocel-T.

8. Change in Number of Ulcers and Ulcer Size

The size of the largest ulcer in the target lower limb as well as the total number of ulcers in both legs was recorded in the Case Report Form (CRF). Ulcer healing and changes in ulcer size from baseline to Months 1, 3, 6, 9 and 12 was assessed.

9. Vasculogenesis

Vasculogenesis was assessed at Month 6 after the administration of the cell suspension of the invention by an Evaluation Committee formed by two interventional radiologists who performed an independent, blind evaluation by comparing the baseline angiogram performed before treatment with the angiogram performed at 6 Months post-administration Rexmyelocel-T.

Vasculogenesis was considered to have occurred if a longitudinal growth of preexisting arteries, cross growth of preexisting arteries, increase in the number of collateral blood vessels, increase in the number of collateral blood vessels, increase in size and/or density of collateral blood vessels or increase in the size and/or density of major infra-popliteal vessels was presented.

10. Major Amputations (Target Limb)

Major amputation was considered as an amputation of the lower limb above the ankle.

11. Change in ABI

ABI is defined as the ratio of the systolic blood pressure measured at the ankle to that measured at the brachial artery. The subject was instructed to rest for 5 to 10 min in the supine position, relaxed, head and heels supported, in a room at a temperature of 19° C.-22° C. An appropriately sized blood pressure cuff was selected to measure the blood pressure in both the ankle and the arm. For both the ankle and the arm, the cuff was placed around the limb using the straight wrapping method. An 8- to 10-MHz Doppler probe was used and Doppler gel applied over the sensor. The Doppler probe was also used for the detection of the brachial blood flow during the arm pressure measurement. The brachial systolic pressures of both arms and the anterior tibial and posterior tibial systolic pressures of the extremity in question were measured.

The change in ABI from baseline to Months 1, 3, 6, 9 and 12 was recorded in subjects in whom the ankle pressure could be reliably assessed.

12. Changes in the Transcutaneous Oxygen Pressure

Transcutaneous oximetry, TcPO2, is a local, non-invasive measurement reflecting the amount of O2 that has diffused from the capillaries, through the epidermis. TcPO2 was measured with the TCM3 (Radiometer Medical ApS, Copenhagen, Denmark).

The change in TcPO2 from baseline to Months 1, 3, 6, 9 and 12 was recorded.

13. Adverse Event Definitions

Adverse events (AEs) were defined as any undesirable experience occurring to a subject during the trial, whether or not considered related to the investigational product. An AE could therefore be any unfavorable and unintended sign (including an abnormal laboratory finding), symptom, or disease temporally associated with the use of a medicinal (investigational) product, whether or not it was related to the medicinal (investigational) product. This included an exacerbation of preexisting conditions or events, inter-current illnesses, drug interaction or the significant worsening of the indication under investigation that was not recorded elsewhere in the case report form under specific efficacy assessments. Anticipated fluctuations of preexisting conditions, including the disease under study that do not represent a clinically significant exacerbation or worsening were not considered to be AEs.

The following data were documented for each AE:
Description of the symptom event.
Classification of 'serious' or 'not serious'.
Severity: mild (an AE that is easily tolerated by the subject, causes minimal discomfort and does not interfere with everyday activities), moderate (an AE that is sufficiently discomforting to interfere with normal everyday activities; intervention may be needed),
severe (an AE that prevents normal everyday activities; treatment or other intervention usually needed).
Date of first occurrence and date of resolution (if applicable).
Action taken: any action, permanent discontinuation of trial treatment, administration of concomitant medication, management of non-pharmacological treatment or hospitalization/prolonged hospitalization (SAE).
Causal relationship. Every effort was made by the Investigator to assess the relationship of the AE, if any, to the Rexmyelocel-T. Causality was assessed using the following categories:
Unlikely, if there was little evidence to suggest a causal relationship (e.g. the event did not occur in a reasonable period of time after administration of Rexmyelocel-T, or if there was another reasonable explanation for the event (e.g. the subject's clinical condition, other concomitant treatments). Possible, if there is evidence to suggest a possible causal relationship (e.g. because the event occurred within a reasonable time after administration of Rexmyelocel-T, even though, other factors may have contributed to the event (e.g. the subject's clinical condition, other concomitant treatments). Probable, if there is evidence to suggest a causal relationship and the influence of other factors is unlikely.
Certain, if there is clear evidence to suggest a causal relationship and a possible contribution of other factors can be ruled out
Unreadable, if there is insufficient or incomplete evidence to make a clinical judgment on a causal relationship.
Outcome of event (unknown, recovered, not yet recovered, recovered with sequelae, death (with date and cause reported)).

14. Serious Adverse Event Definition

A SAE was defined as an AE that met one or more of the following serious outcome criteria:
Resulted in death.
Was life threatening.
Required inpatient hospitalization or prolongation of an existing hospitalization.
Resulted in persistent or significant disability or incapacity.
Was a congenital anomaly or birth defect.
Was an important medical event that, based on medical and scientific judgment, had the potential to jeopardize the subject or required intervention to prevent one of the outcomes listed above.

AE was considered to be life threatening if the subject was at risk of death at the time of the event. It was not considered an event that in theory could have been the cause of death if it had been more severe.

Example 2. Results

1. Change in Rutherford Classification

The change in Rutherford Category of PAD in control subjects and in subjects treated with the cell suspension of the invention is at baseline and after 3, 6, 9, and 12 months is presented in Table 7 below.

At the Baseline Visit, subjects in the cell suspension of the invention treatment groups were classified as CLI Rutherford Category 4 (Grade II) or Rutherford Category 5 (Grade III) (20 (44%) subjects and 25 (56%) subjects, respectively. Results showed that within the first 12 months, the majority of subjects treated with the cell suspension of the invention achieved a clinically relevant response as demonstrated by an improvement i.e., reduction in their classification to Rutherford Category 0-3 (Grade 0 and 1) in 28 (68%) subjects.

Three months after the administration, 15 (33%) subjects treated with the cell suspension of the invention and 12 (40%) subjects in the middle and high dose groups no longer suffered from rest pain or tissue loss and were classified as Rutherford Category 0-3, (Grade 0 and I) which further increased to 21 (46%) subjects, 24 (57%) and 28 (68%) at 6, 9 and 12-months post-administration, respectively. For subjects in the middle and high dose groups this was 13 (43%), 15 (50%) and 18 (64%) at 6, 9 and 12-months post-administration, respectively. This compared favorably to the control group, in which 0 (0%), 1 (8%), 1 (8%) and 2 (18%) subjects improved to Rutherford Category 1-3, (Grade I) after 3, 6, 9 and 12 months, respectively.

One subject assigned to the control group withdrew informed consent following randomization, one subject died due to cardiovascular disease before the 6-month Follow-up Visit, one patient had undergone a major amputation before the Month 6-month Follow-up Visit, and one subject was

TABLE 7

Rutherford classification at baseline and months 3, 6, 9, and 12 after Rexmyelocel-T administration

| Category | Grade | Control (n, %) | Lowest Dose $1 \times 10^8$ BM-MNCs (n, %) | Middle Dose $5 \times 10^8$ BM-MNCs (n, %) | Highest Dose $1 \times 10^9$ BM-MNCs (n, %) | All treated subjects (n, %) |
|---|---|---|---|---|---|---|
| Baseline | | | | | | |
| 0 | 0 | 0 | 0 | 0 | 0 | 0 |
| 1-3 | I | 0 | 0 | 0 | 0 | 0 |
| 4 | II | 6 (40) | 7 (47) | 7 (47) | 6 (40) | 20 (44) |
| 5 | III | 9 (60) | 8 (53) | 8 (53) | 9 (60) | 25 (56) |
| 6 | IV | 0 | 0 | 0 | 0 | 0 |
| Total | | 15 | 15 | 15 | 15 | 45 |
| 3-months | | | | | | |
| 0 | 0 | 0 | 0 | 0 | 0 | 0 |
| 1-3 | I | 0 | 3 (20) | 6 (40) | 6 (40) | 15 (33) |
| 4 | II | 7 (50) | 6 (40) | 3 (20) | 1 (7) | 10 (22) |
| 5 | III | 6 (43) | 6 (40) | 6 (40) | 8 (53) | 20 (44) |
| 6 | IV | 1 (7) | 0 | 0 | 0 | 0 |
| Total | | 14 | 15 | 15 | 15 | 45 |
| 6-months | | | | | | |
| 0 | 0 | 0 | 0 | 1 (7) | 0 | 1 (2) |
| 1-3 | I | 1 (8) | 7 (47) | 6 (40) | 7 (47) | 20 (44) |
| 4 | II | 7 (58) | 5 (33) | 3 (20) | 0 (0) | 8 (18) |
| 5 | III | 3 (25) | 3 (20) | 5 (33) | 8 (53) | 16 (36) |
| 6 | IV | 1 (8) | 0 | 0 | 0 | 0 |
| Total | | 12 | 15 | 15 | 15 | 45 |
| 9-months | | | | | | |
| 0 | 0 | 0 | 0 | 0 | 0 | 0 |
| 1-3 | I | 1 (8) | 9 (69) | 8 (57) | 7 (47) | 24 (57) |
| 4 | II | 7 (58) | 2 (15) | 2 (14) | 2 (13) | 6 (14) |
| 5 | III | 3 (25) | 2 (15) | 4 (29) | 6 (40) | 12 (29) |
| 6 | IV | 1 (8) | 0 | 0 | 0 | 0 |
| Total | | 12 | 13 | 14 | 15 | 42 |
| 12-months | | | | | | |
| 0 | 0 | 0 | 0 | 2 (14) | 0 | 2 (5) |
| 1-3 | I | 2 (18) | 10 (77) | 9 (64) | 7 (50) | 26 (63) |
| 4 | II | 5 (46) | 0 | 2 (14) | 5 (36) | 7 (17) |
| 5 | III | 4 (36) | 3 (23) | 1 (7) | 2 (14) | 6 (15) |
| 6 | IV | 0 | 0 | 0 | 0 | 0 |
| Total | | 11 | 13 | 14 | 14 | 41 |

Abbreviations:
BMNCs = Bone marrow-derived mononuclear cells lost to follow-up before the Month 12 visit. Two subjects who had received the lower dose of Rexmyelocel-T underwent a major amputation after six months' post administration in the target limb.

A total of 28 of 45 (62%) subjects in the cell suspension of the invention treatment groups at 12-months post-administration, of which 18 of 30 (63%) in the middle and high dose groups did not present with ischemic pain at rest or with ischemic ulcers compared with the control group where 9 of 11 (82%) subjects reported rest pain or the presence of non-healing ischemic ulcers (4 (36%) subjects).

Figure 2:
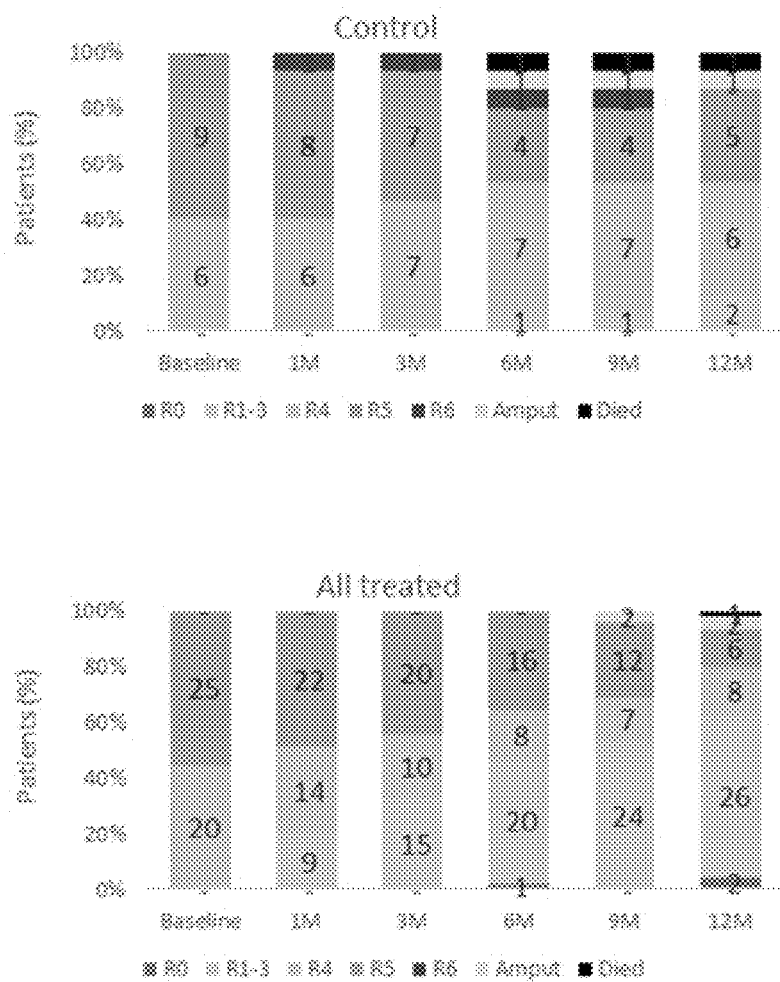
FIG. 2. Rutherford classification at 3, 6, 9 and 12 months after the cell suspension of the invention administration, control versus treated (included amputated and deaths) LOCF.
Figure 3:
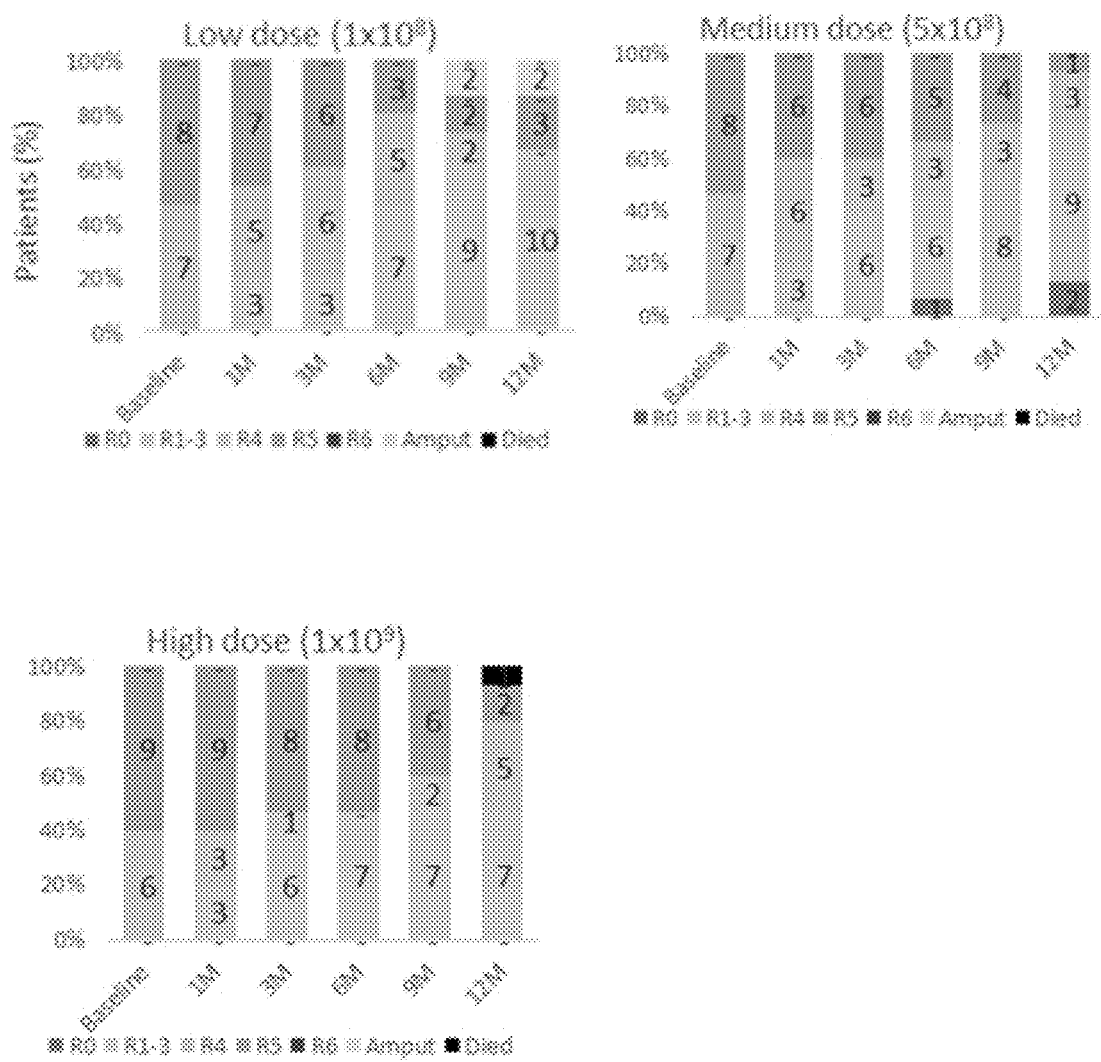
FIG. 3. Rutherford classification at 3, 6, 9 and 12 months after the cell suspension of the invention administration, effect of three escalating doses (including amputations and deaths) LOCF.

When the last observation carried forward (LOCF) is applied (excluding subjects with major limb amputation; these subjects were considered to be non-responders), results indicated that within the first 12 months post the cell suspension of the invention administration, a clinically relevant response was achieved as demonstrated by a reduction in their classification to Rutherford. Category 0-3 (Grade 0 and I) in 28 (64%) of all treated subjects and 18 (63%) in the middle and high dose groups (see Table 8 and FIG. 2 and FIG. 3).

Three months after the administration of Rexmyelocel-T, 15 (33%) subjects treated with Rexmyelocel-T, of which 12 (40%) in the middle and high dose groups no longer suffered from rest pain or tissue loss and were classified as Rutherford Category 0-3, (Grade 0 and I) which further increased to 21 (46%) subjects and 24 (53%) subjects at 6 and 9 months post-administration, respectively for all treated patients. In the middle and high dose groups 14 (47%) and 15 (50%) subjects were classified as Rutherford Category 0-3 at 6 and 9 months respectively. This compared favorably to the control group, in which only 0 (0%), one (8%), 1 (7%) and two (13%) subjects improved to Rutherford Category 1-3, (Grade I) after 3, 6, 9 and 12 months, respectively.

TABLE 8

Rutherford classification at baseline and 3, 6, 9 and 12 months after Rexmyelocel-T administration (including amputations and deaths)-LOCF

| Category | Grade | Control (N, %) | Low Dose $1 \times 10^8$ BM-MNCs (N, %) | Middle Dose $5 \times 10^8$ BM-MNCs (N, %) | High Dose $1 \times 10^9$ BM-MNCs (N, %) | All treated subjects (N, %) |
|---|---|---|---|---|---|---|
| Baseline | | | | | | |
| 0 | 0 | 0 | 0 | 0 | 0 | 0 |
| 1-3 | I | 0 | 0 | 0 | 0 | 0 |
| 4 | II | 6 (40) | 7 (47) | 7 (47) | 6 (40) | 20 (44) |
| 5 | III | 9 (60) | 8 (53) | 8 (53) | 9 (60) | 25 (56) |
| 6 | IV | 0 | 0 | 0 | 0 | 0 |
| Amputated | | 0 | 0 | 0 | 0 | 0 |
| Died | | 0 | 0 | 0 | 0 | 0 |
| Total | | 15 | 15 | 15 | 15 | 45 |
| 3-months | | | | | | |
| 0 | 0 | 0 | 0 | 0 | 0 | 0 |
| 1-3 | I | 0 | 3 (20) | 6 (40) | 6 (40) | 15 (33) |
| 4 | II | 7 (47) | 6 (40) | 3 (20) | 1 (7) | 10 (22) |
| 5 | III | 7 (47) | 6 (40) | 6 (40) | 8 (53) | 20 (44) |
| 6 | IV | 1 (6) | 0 | 0 | 0 | 0 |
| Amputated | | 0 | 0 | 0 | 0 | 0 |
| Died | | 0 | 0 | 0 | 0 | 0 |
| Total | | 15 | 15 | 15 | 15 | 45 |
| 6-months | | | | | | |
| 0 | 0 | 0 | 0 | 1 (7) | 0 | 1 (2) |
| 1-3 | I | 1 (7) | 7 (47) | 6 (40) | 7 (47) | 20 (44) |
| 4 | II | 7 (47) | 5 (33) | 3 (20) | 0 | 8 (18) |
| 5 | III | 4 (27) | 3 (20) | 5 (33) | 8 (53) | 16 (36) |
| 6 | IV | 1 (7) | 0 | 0 | 0 | 0 |
| Amputated | | 1 (7) | 0 | 0 | 0 | 0 |
| Died | | 1 (7) | 0 | 0 | 0 | 0 |
| Total | | 15 | 15 | 15 | 15 | 45 |
| 9-months | | | | | | |
| 0 | 0 | 0 | 0 | 0 | 0 | 0 |
| 1-3 | I | 1 (7) | 9 (60) | 8 (53) | 7 (47) | 24 (53) |
| 4 | II | 7 (47) | 2 (20) | 3 (20) | 2 (13) | 8 (18) |
| 5 | III | 4 (27) | 2 (20) | 4 (27) | 6 (40) | 13 (29) |
| 6 | IV | 1 (7) | 0 | 0 | 0 | 0 |
| Amputated | | 1 (7) | 2 (13) | 0 | 0 | 2 (4) |
| Died | | 1 (7) | 0 | 0 | 0 | 0 |
| Total | | 15 | 15 | 15 | 15 | 45 |
| 12-months | | | | | | |
| 0 | 0 | 0 | 0 | 2 (13) | 0 | 2 (4) |
| 1-3 | I | 2 (13) | 10 (67) | 9 (60) | 7 (50) | 26 (58) |
| 4 | II | 6 (40) | 0 (7) | 3 (20) | 5 (36) | 8 (18) |
| 5 | III | 5 (33) | 3 (27) | 1 (7) | 2 (14) | 6 (13) |
| 6 | IV | 0 | 0 | 0 | 0 | 0 |

TABLE 8-continued

Rutherford classification at baseline and 3, 6, 9 and 12 months after
Rexmyelocel-T administration (including amputations and deaths)-LOCF

| Category | Grade | Control (N, %) | Low Dose $1 \times 10^8$ BM-MNCs (N, %) | Middle Dose $5 \times 10^8$ BM-MNCs (N, %) | High Dose $1 \times 10^9$ BM-MNCs (N, %) | All treated subjects (N, %) |
|---|---|---|---|---|---|---|
| Amputated | | 1 (7) | 2 (13) | 0 | 0 | 2 (4) |
| Died | | 1 (7) | 0 | 0 | 1 (7) | 1 (2) |
| Total | | 15 | 15 | 15 | 15 | 45 |

Abbreviations:
BMNCs = Bone marrow-derived mononuclear cells

Figure 4:
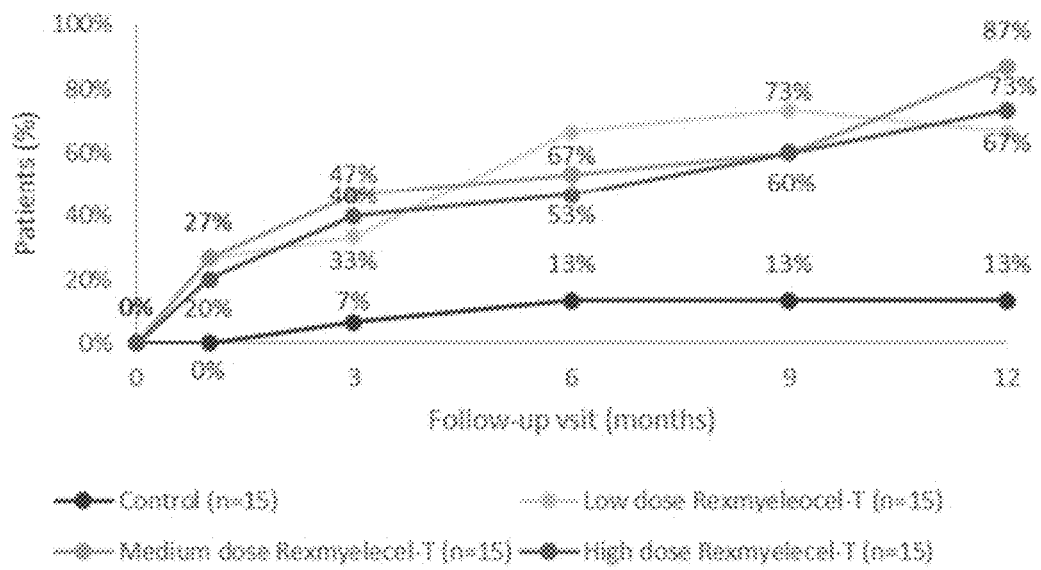
FIG. 4. Improvement in Rutherford classification (percentage of subjects) 3, 6, 9 and 12 months for control group and three groups (doses) of the cell suspension of the invention.

FIG. 4 and Table 9 showed a clinically relevant response in more subjects in the cell suspension of the invention treatment groups compared with the control group at all post administration follow-up visits. By 12 months post administration of Rexmyelocel-T the majority of subjects in all Rexmyelocel-T groups demonstrated a clinically relevant response compared to the control group: 34 (76%) subjects (10, 13, and 11 subjects in the lowest, middle, highest Rexmyelocel-T groups, respectively) versus 2 (13%) subjects.

one ulcer and there were no major differences between the treatment and control groups (5, 7, and 6 subjects in the lowest, middle, highest cell suspension of the invention groups, respectively and 6 subjects in the control group). Four subjects in the lowest, middle, highest cell suspension of the invention treatment groups (1, 1, and 2 subjects, respectively) and one subject in the control group had 3 ulcers.

Although the average ulcer size at baseline in subjects in the cell suspension of the invention treatment group was

TABLE 9

Rutherford classification) at 3, 6, 9 and 12 months
after Rexmyelocel-T administration-LOCF

| | Control (N, %) | Lowest Dose $1 \times 10^8$ BM-MNCs (N, %) | Middle Dose $5 \times 10^8$ BM-MNCs (N, %) | Highest Dose $1 \times 10^9$ BM-MNCs (N, %) | All treated subjects (N,%) |
|---|---|---|---|---|---|
| 3-months | | | | | |
| Response | 1 (7) | 5 (33) | 7 (47) | 6 (40) | 18 (40) |
| Maintain | 13 (87) | 10 (67) | 8 (53) | 9 (60) | 27 (60) |
| Non-response | 1 (7) | 0 | 0 | 0 | 0 |
| Total | 15 | 15 | 15 | 15 | 45 |
| 6-months | | | | | |
| Response | 2 (13) | 10 (67) | 8 (53) | 7 (47) | 25 (56) |
| Maintain | 11 (73) | 5 (33) | 7 (47) | 7 (47) | 19 (42) |
| Non-response | 2 (13) | 0 | 0 | 1 (7) | 1 2) |
| Total | 15 | 15 | 15 | 15 | 45 |
| 9-months | | | | | |
| Response | 2 (13) | 11 (73) | 9 (60) | 9 (60) | 29 (64) |
| Maintain | 11 (73) | 4 (27) | 6 (40) | 5 (33) | 15 (33) |
| Non-response | 2 (13) | 0 | 0 | 1 (7) | 1 (2) |
| Total | 15 | 15 | 15 | 15 | 45 |
| 12-months | | | | | |
| Response | 2 (13) | 10 (67) | 13 (87) | 12 (80) | 35 (78) |
| Maintain | 12 (80) | 5 (33) | 2 (13) | 3 (20) | 7 (22) |
| Non-response | 1 (7) | 0 | 0 | 0 | 0 |
| Total | 15 | 15 | 15 | 15 | 45 |

Abbreviations: BMNCs = Bone marrow-derived mononuclear cells

2. Change in the Number of Ulcers in the Affected Limb

Figure 5:
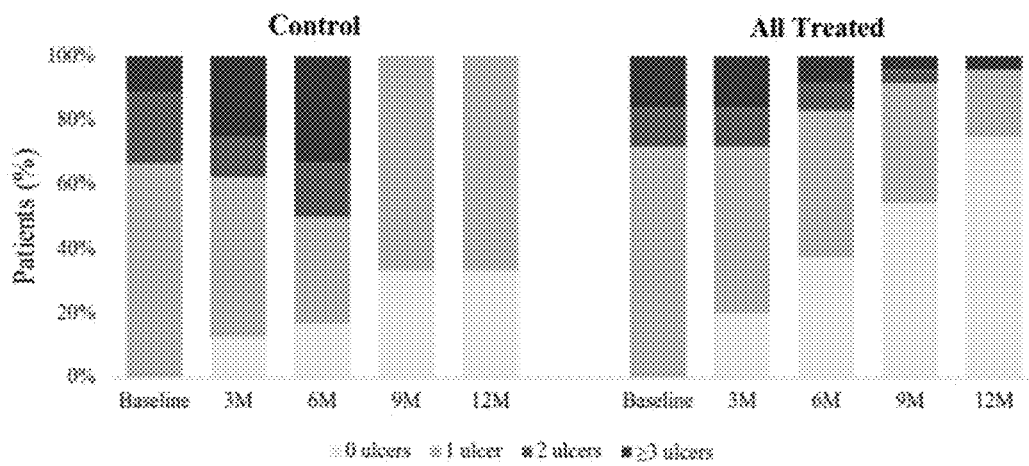
FIG. 5. Proportion of subjects classified by number of ulcers in the affected limb at 3, 6, 9 and 12 months (left panel: control group; right panel cell suspension of the invention group).

The change in the number of ulcers in the affected limb is presented in Table 10 and FIG. 5. At the Baseline Visit, 25 subjects (56%) in the cell suspension of the invention treatment groups and 9 subjects (60%) in the control group were classified as Rutherford Category 5 and presented with non-healing ischemic ulcers. The majority of subjects had higher than that for subjects in the control group (39.9±23.0 mm versus 26.3±23.5 mm in the treated and control groups, respectively), the results showed that in subjects in whom the ulcer did not heal, the ulcer size decreased (29.7±13.5 mm), while the mean ulcer size increased in the control group (43.8±29.3 mm) (Table 11).

TABLE 10

Change in the number of ulcers in the affected limb

| | Control (n, %) | Lowest Dose $1 \times 10^8$ BM-MNCs (n, %) | Middle Dose $5 \times 10^8$ BM-MNCs (n, %) | Highest Dose $1 \times 10^9$ BM-MNCs (n, %) | All treated subjects (n, %) |
|---|---|---|---|---|---|
| Baseline | | | | | |
| 0 ulcer | | | | | |
| 1 ulcer | 6 (67) | 5 (63) | 7 (88) | 6 (67) | 18 (72) |
| 2 ulcers | 2 (22) | 2 (25) | 0 | 1 (11) | 3 (12) |
| ≥3 ulcers | 1 (11) | 1 (12) | 1 (12) | 2 (22) | 4 (16) |
| Total | 9 | 8 | 8 | 9 | 25 |
| 3-months post Rexmyelocel-T administration | | | | | |
| 0 ulcer | 1 (13) | 2 (25) | 2 (25) | 1 (11) | 5 (20) |
| 1 ulcer | 4 (50) | 4 (50) | 5 (63) | 4 (44) | 13 (52) |
| 2 ulcers | 1 (12) | 0 | 0 | 3 (33) | 3 (12) |
| ≥3 ulcers | 2 (25) | 2 (25) | 1 (12) | 1 (11) | 4 (16) |
| Total | 8 | 8 | 8 | 9 | 25 |
| 6-months post Rexmyelocel-T administration | | | | | |
| 0 ulcer | 2 (33) | 4 (57) | 3 (38) | 2 (22) | 9 (38) |
| 1 ulcer | 4 (67) | 1 (14) | 4 (50) | 6 (67) | 11 (46) |
| 2 ulcers | 0 | 2 (29) | 0 | 0 | 2 (8) |
| ≥3 ulcers | 0 | 0 | 1 (12) | 1 (11) | 2 (8) |
| Total | 6 | 7 | 8 | 9 | 24 |
| 9-months post Rexmyelocel-T administration | | | | | |
| 0 ulcer | 2 (33) | 5 (71) | 4 (50) | 4 (44) | 13 (54) |
| 1 ulcer | 4 (67) | 2 (29) | 3 (38) | 4 (44) | 9 (38) |
| 2 ulcers | 0 | 0 | 0 | 1 (11) | 1 (4) |
| ≥3 ulcers | 0 | 0 | 1 (12) | 0 | 1 (4) |
| Total | 6 | 7 | 8 | 9 | 24 |
| 12-months post Rexmyelocel-T administration | | | | | |
| 0 ulcer | 2 (33) | 4 (57) | 7 (88) | 7 (78) | 18 (75) |
| 1 ulcer | 4 (66) | 3 (43) | 0 | 2 (22) | 5 (21) |
| 2 ulcers | 0 | 0 | 0 | 0 | 0 |
| ≥3 ulcers | 0 | 0 | 1 (12) | 0 | 1 (4) |
| Total | 6 | 7 | 8 | 9 | 24 |

TABLE 11

Ulcer size in the affected limb (largest diameter)

| | Control (n = 15) | Lowest Dose $1 \times 10^8$ BM-MNCs (n = 15) | Middle Dose $5 \times 10^8$ BM-MNCs (n = 15) | Highest Dose $1 \times 10^9$ BM-MNCs (n = 15) | All treated subjects (n = 45) |
|---|---|---|---|---|---|
| Baseline | | | | | |
| N | 9 | 8 | 7 | 8 | 23 |
| Mean ± SD | 26.3 ± 23.5 | 41.5 ± 29.1 | 31.4 ± 19.7 | 45.6 ± 19.2 | 39.9 ± 23.0 |
| 3 months | | | | | |
| N | 5 | 6 | 6 | 7 | 19 |
| Mean ± SD | 21.8 ± 17.9 | 51.7 ± 39.7 | 23.7 ± 19.5 | 27.9 ± 12.9 | 34.1 ± 27.4 |

TABLE 11-continued

Ulcer size in the affected limb (largest diameter)

| | Control (n = 15) | Lowest Dose $1 \times 10^8$ BM-MNCs (n = 15) | Middle Dose $5 \times 10^8$ BM-MNCs (n = 15) | Highest Dose $1 \times 10^9$ BM-MNCs (n = 15) | All treated subjects (n = 45) |
|---|---|---|---|---|---|
| 6 months | | | | | |
| N | 3 | 4 | 5 | 7 | 16 |
| Mean ± SD | 36.7 ± 15.3 | 42.5 ± 43.5 | 24.0 ± 19.8 | 24.3 ± 13.7 | 28.8 ± 25.0 |
| 9 months | | | | | |
| N | 3 | 2 | 4 | 5 | 11 |
| Mean ± SD | 26.7 ± 5.8 | 27.5 ± 17.7 | 12.5 ± 6.5 | 23.0 ± 14.8 | 20.0 ± 13.0 |
| 12 months | | | | | |
| N | 4 | 3 | 1 | 2 | 6 |
| Mean ± SD | 43.8 ± 29.3 | 31.7 ± 17.6 | 15.0* | 34.0 ± 35.7 | 29.7 ± 13.5 |

*At 12 months one subject in the middle dose presented with an ulcer on the affected limb. The actual size of this ulcer is presented.

3. Change in TcPO2

The change in TcPO2 is presented in Table 12.

At baseline, 35 (79%) subjects in the cell suspension of the invention treatment groups had a TcPO2<40 mmHg (12, 12, and 11 subjects in the three dose groups (lowest, middle, highest groups, respectively) compared with 6 (43%) subjects in the control group.

Results showed that by the Month 12 Follow-up Visit, TcPO2 levels increased to 40 mmHg in the majority of subjects treated with Rexmyelocel-T (24 (60%) subjects) compared with 5 (46%) subjects in the control group.

TABLE 12

Change in transcutaneous oxygen pressure

| | Control (N, %) | Lowest Dose $1 \times 10^8$ BM-MNCs (N, %) | Middle Dose $5 \times 10^8$ BM-MNCs (N, %) | Highest Dose $1 \times 10^9$ BM-MNCs (N, %) | All treated subjects (N, %) |
|---|---|---|---|---|---|
| Baseline | | | | | |
| $TcO_2 \geq 40$ mmHg | 8 (57) | 2 (14) | 3 (20) | 4 (27) | 9 (21) |
| $TcO_2 < 40$ mmHg | 6 (43) | 12 (86) | 12 (80) | 11 (73) | 35 (79) |
| Total | 14 | 14 | 15 | 15 | 44 |
| 3-months post Rexmyelocel-T administration | | | | | |
| $TcO_2 \geq 40$ mmHg | 7 (64) | 6 (43) | 6 (43) | 8 (53) | 20 (47) |
| $TcO_2 < 40$ mm Hg | 4 (36) | 8 (57) | 8 (57) | 7 (47) | 23 (53) |
| Total | 11 | 14 | 14 | 15 | 43 |
| 6-months post Rexmyelocel-T administration | | | | | |
| $TcO_2 \geq 40$ mmHg | 6 (55) | 7 (47) | 5 (39) | 8 (53) | 20 (47) |
| $TcO_2 < 40$ mmH | 5 (45) | 8 (53) | 8 (61) | 7 (47) | 23 (53) |
| Total | 11 | 15 | 13 | 15 | 43 |
| 12-months post Rexmyelocel-T administration | | | | | |
| $TcO_2 \geq 40$ mmHg | 5 (46) | 9 (69) | 7 (54) | 8 (57) | 24 (60) |
| $TcO_2 < 40$ mmHg | 6 (54) | 4 (31) | 6 (46) | 6 (43) | 16 (40) |
| Total | 11 | 13 | 13 | 14 | 40 |

4. Vasculogenesis

Vasculogenesis was assessed at Month 6 post administration of the cell suspension of the invention. In subjects treated with the cell suspension of the invention, vasculogenesis was present in 26 (62%) subjects: 7, 8, and 9 subjects in the lowest, middle, highest groups, respectively (see Table 13).

TABLE 13

| | Lowest Dose $1 \times 10^8$ BM-MNCs (n, %) | Middle Dose $5 \times 10^8$ BM-MNCs (n, %) | Highest Dose $1 \times 10^9$ BM-MNCs (n, %) | All treated subjects (n, %) |
|---|---|---|---|---|
| Vasculogenesis | | | | |
| 6-months post Rexmyelocel-T administration | | | | |
| Vasculogenesis | 7 (58) | 8 (62) | 9 (64) | 24 (62) |
| Non vasculogenesis | 5 (42) | 5 (38) | 5 (36) | 15 (38) |
| Total | 12 | 13 | 14 | 39 |

Figure 6:
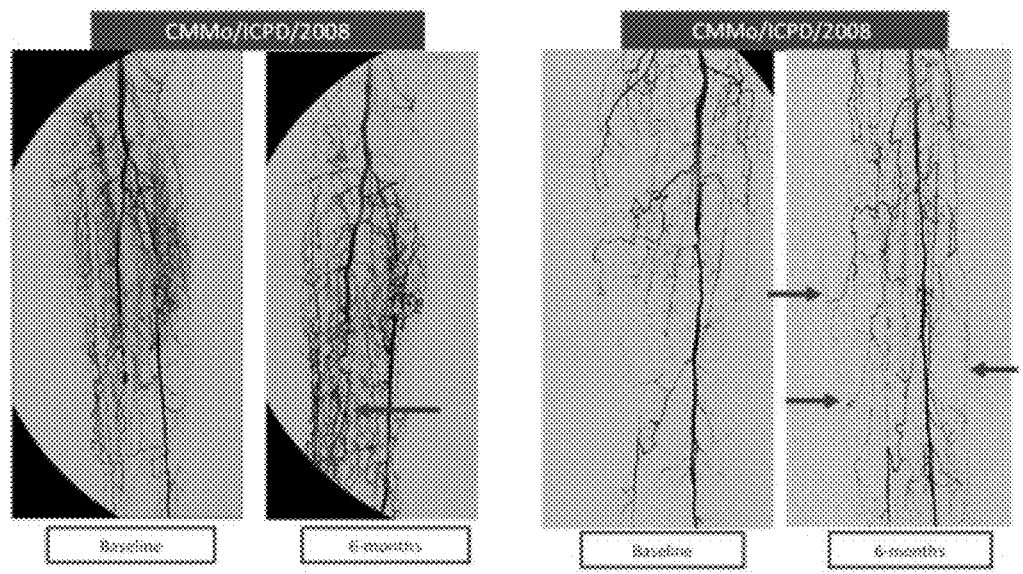
FIG. 6. Angiographic images of three of the 24 cases of vasculogenesis that occurred are presented relative to baseline in FIG. 6: a longitudinal growth of arteries (FIG. 6A), appearance the new vessels (FIG. 6B) and transverse growth of collateral that target skin (FIG. 6C).
Figure 6:
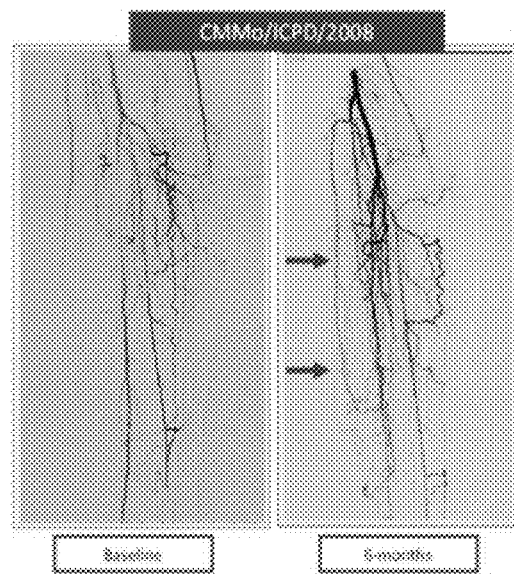
Figure 7:
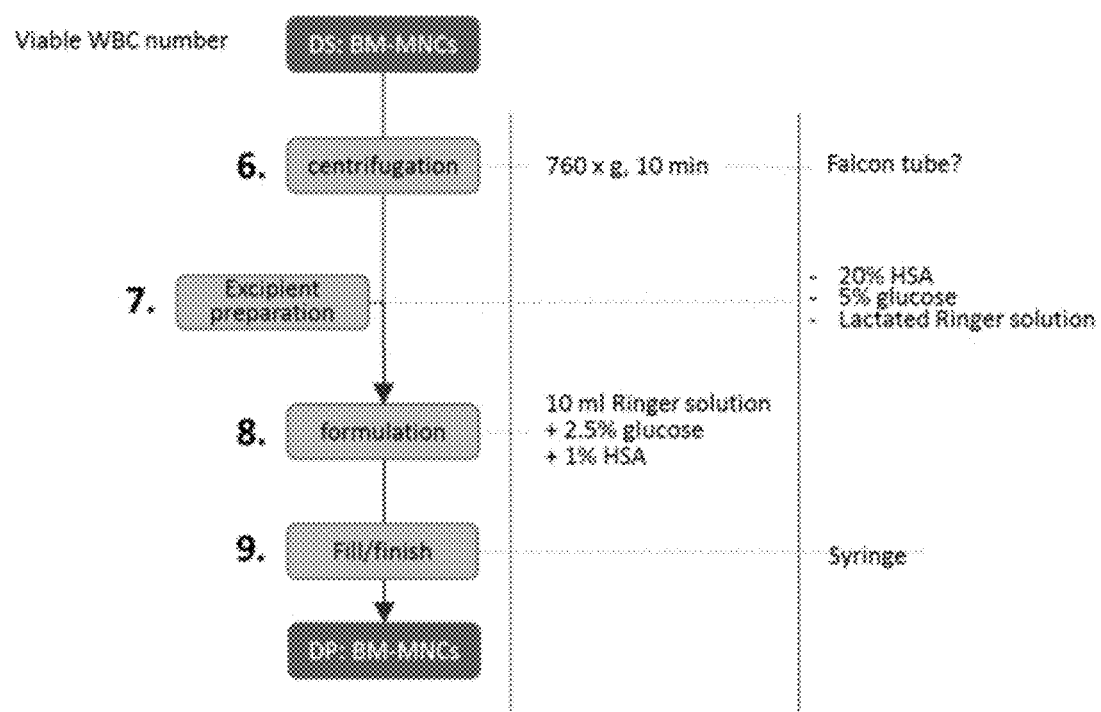
FIG. 7. Flow chart of cell suspension of the invention product manufacturing process.

Angiographic images of three of the 24 cases of vasculogenesis that occurred are presented relative to baseline in FIG. 6: a longitudinal growth of arteries (FIG. 6A), appearance the new vessels (FIG. 6B) and transverse growth of collateral that target skin (FIG. 6C).

The invention claimed is:

1. A cell suspension comprising from $4 \times 10^8$ to $1.2 \times 10^9$ white blood cells derived from the bone marrow of a human subject, wherein of the total number of from $4 \times 10^8$ to $1.2 \times 10^9$ white blood cells:
   i. 20% to 51% are lymphocytes, and 3.9% to 22.3% are monocytes;
   ii. 1.4% to 10% are hematopoietic stem cells that express CD34;
   iii. 25.3% to 83.3% of the total number of white blood cells are mononuclear cells;
   iv. 16.7% to 74.7% of the total number of white blood cells are granulocytes;
   v. 5.4% to 38.8% of the total number of white blood cells express CXCR4;
   vi. 0.07% to 24.7% of total number of white blood cells express VEGFR2;
   vii. of the total number of hematopoietic stem cells that express CD34, 7.7% to 55.5% are early, non-committed hematopoietic stem cells that do not express CD38 and 0.7% to 10.3% are stem cells that express CXCR4; and
   viii. the maximum ratio of red blood cells to leucocyte cells is 6.7 and the maximum ratio of platelets to leucocyte cells is 32;
   wherein the cell suspension is for use in the treatment or amelioration of lower extremity peripheral artery disease; and wherein the cell suspension is derived from the same subject that is intended to receive the cell suspension or is derived from a different subject that is intended to receive the cell suspension.

2. The cell suspension according to claim 1, wherein of the total number of white blood cells, 32.3% to 80.0% are mononuclear cells selected from the list consisting of lymphocytes, monocytes and hematopoietic stem cells that express CD34 and 20.0% to 67.7% are granulocytes.

3. The cell suspension according to claim 1, wherein the cell suspension comprises $5 \times 10^8$ to $1.2 \times 10^9$ white blood cells derived from the bone marrow of a human subject.

4. The cell suspension according to claim 1, wherein the cell suspension comprises $8 \times 10^8$ to $1.2 \times 10^9$ white blood cells derived from the bone marrow of a human subject.

5. The cell suspension according to claim 1, wherein the cell suspension comprises $9 \times 10^8$ to $1.1 \times 10^9$ white blood cells derived from the bone marrow of a human subject.

6. The cell suspension according to claim 1, wherein the cell suspension comprises $9.5 \times 10^8$ to $1.05 \times 10^9$ white blood cells derived from the bone marrow of a human subject.

7. The cell suspension according to claim 1, wherein the cell suspension comprises $9.8 \times 10^8$ to $1.02 \times 10^9$ white blood cells derived from the bone marrow of a human subject.

8. The cell suspension according to claim 1, wherein the lower extremity peripheral artery disease is critical limb ischemia.

9. The cell suspension according to claim 1, wherein the cells of such cell suspension are suspended in a volume of from 5 to 30 ml of a heparinized saline solution or lactated Ringer solution, comprising about 1% HSA and about 2.5% glucose.

10. One or several pre-filled syringe/s comprising a cell suspension as defined in claim 1.

11. The syringe/S according to claim 10, wherein said suspension is provided as a single dose.

* * * * *

UNITED STATES PATENT AND TRADEMARK OFFICE
CERTIFICATE OF CORRECTION

PATENT NO.            : 10,869,886 B2
APPLICATION NO.       : 15/688555
DATED                 : December 22, 2020
INVENTOR(S)           : Jonathan Robert Barclay Dupere et al.

Page 1 of 1

It is certified that error appears in the above-identified patent and that said Letters Patent is hereby corrected as shown below:

On the Title Page

Please change:
"(73) Assignees: REXGENERO BIOSCIENCES S.L., Seville (ES);
SERVICIO ANDALUZ DE SALUD, Seville (ES);
FUNDACIÜBLICA ANDALUZA PROGRESO Y SALUD, Seville (ES)"

To:
-- (73) Assignees: REXGENERO BIOSCIENCES S.L., Seville (ES);
SERVICIO ANDALUZ DE SALUD, Seville (ES);
FUNDACIÓN PÚBLICA ANDALUZA PROGRESO Y SALUD, Seville (ES) --

Signed and Sealed this
Twenty-third Day of February, 2021

Drew Hirshfeld
*Performing the Functions and Duties of the
Under Secretary of Commerce for Intellectual Property and
Director of the United States Patent and Trademark Office*